United States Patent [19]

Miljanich et al.

[11] Patent Number: 5,559,095
[45] Date of Patent: * Sep. 24, 1996

[54] DELAYED TREATMENT METHOD OF REDUCING ISCHEMIA-RELATED NEURONAL DAMAGE

[75] Inventors: George P. Miljanich, Redwood; Stephen S. Bowersox, Menlo Park; James A. Fox, Palo Alto; Karen L. Valentino, San Carlos, all of Calif.; Robert S. Bitner, West Lafayette, Ind.; Donald H. Yamashiro, Cleveland Heights, Ohio

[73] Assignee: Neurex Corporation, Menlo Park, Calif.

[*] Notice: The portion of the term of this patent subsequent to Sep. 24, 2018, has been disclaimed.

[21] Appl. No.: 789,913

[22] Filed: Nov. 12, 1991

Related U.S. Application Data

[63] Continuation-in-part of Ser. No. 561,766, Aug. 2, 1990, Pat. No. 5,189,020, which is a continuation-in-part of Ser. No. 440,094, Nov. 22, 1989, Pat. No. 5,051,403.

[51] Int. Cl.$^6$ .................................................. A61K 38/16
[52] U.S. Cl. .............................. 514/12; 514/13; 530/324; 530/325; 530/326
[58] Field of Search ................................. 514/12, 13–15, 514/21; 530/350, 324, 325, 326, 327

[56] References Cited

U.S. PATENT DOCUMENTS

5,051,403  9/1991  Miljanich .................................. 514/12

OTHER PUBLICATIONS

Olivera et al, *Biochemistry* 26, 2086, 1987.
Feuerstein et al. *J. Pharmacol Exp Ther* 252, 778, 1990.
Ahmad, S., and G. P. Miljanich, "The calcium channel antagonist, ω–conotoxin, and electric organ nerve terminals: binding and inhibition of transmitter release and calcium influx," *Brain Research* 453:247–256 (1988).
Bielenberg, G. W., et al., "Effects of Nimodipine of Infarct Size and Cerebral Acidosis After Middle Cerebral Artery Occlusion in the Rat," *Stroke* 21:IV90–IV92 (1990).
Buchan, A., and W. A. Pulsinelli, "Hypothermia But Not the N–Methyl–D–Aspartate Antagonist, MK–801, Attenuates Neuronal Damage in Gerbils Subjected to Transient Global Ischemia," *J. Neurosci.* 10:311–316 (1990).
Dirnagl, U., et al., "Pre–and post–treatment with MK–801 but not pretreatment alone reduces neocortical damage after focal cerebral ischemia in the rat," *Brain Res.* 527:62–68 (1990).
Gill, R., et al., "MK–801 is Neuroprotective in Gerbils When Administered During the Post–Ischaemic Period," *Neurosci.* 5(3):847–855 (1988).
Goldberg, M., et al., "N–Methyl–D–Aspartate Receptors Mediate Hypoxic Neuronal Injury in Cortical Culture," *J. Pharmacol. Exp. Therapeutics* 243:784–791 (1987).
Gray, W., et al., "Peptide Toxins From Venomous Conus Snails," *Ann. Rev. Biochem.* 57:665–700 (1988).

Hartley, D., and D. Choi, "Delayed Rescue of N–Methyl–D–Aspartate Receptor–Mediated Neuronal Injury on Cortical Culture," *J. Pharmacol. Exp. Therapeutics* 250:752–758 (1989).
Jacewicz, M., et al., "Continuous Nimodipine Treatment Attenuates Cortical Infarction in Rats Subjected to 24 Hours of Focal Cerebral Ischemia," *J. Cereb. Blood Flow Metab.* 10:89–96 (1990).
Kaplan, B., et al., "Temporal Thresholds for Neocortical Infarction in Rats Subjected to Reversible Focal Cerebral Ischemia," *Stroke* 22:1032–1039 (1991).
Kirino, T., "Delayed Neuronal Death in the Gerbil Hippocampus Following Ischemia," *Brain Res.* 239:57–69 (1932).
McCleskey, E. W., et al., "ω–Conotoxin: Direct and persistent blockade of specific types of calcium channels in neurons but not muscle," *Proc. Natl. Acad. Sci. USA* 84:4327–4331 (1987).
Nedergaard, M., "Neuronal injury in the infarct border: A neuropathological study in the rat," *Acta Neuropathol.* (Berl.) 73:267–274 (1987).
Newberg, L., et al., "Failure of Flunarizine to Improve Cerebral Blood Flow of Neurologic Recovery in a Canine Model of Complete Cerebral Ischemia," *Stroke* 15:666–671 (1984).
Nowycky, M. C., et al., "Three types of neuronal calcium channel with different calcium agonist sensitivity," *Nature* (London) 316:440–443 (1985).
Olivera, B., et al., "Purification and Sequence of a Presynaptic Peptide Toxin from *Conus geographus* Venom," *Biochemistry* 23:5087–5090 (1984).
Pulsinelli, W. A., et al., "A New Model of Bilateral Hemispheric Ischemia in the Unanesthetized Rat," *Stroke* 10:267–272 (1979).
Pulsinelli, W. A., et al. "Temporal Profile of Neuronal Damage in a Model of Transient Forebrain Ischemia," *Ann. Neurol.* 11:491–498 (1982).
Sano, K., et al., "Effects of synthetic ω–conotoxin, a new type $Ca^{2+}$ antagonist, on frog and mouse neuromuscular transmission," *Eur. J. Pharmacol.* 141:235–241 (1987).

(List continued on next page.)

*Primary Examiner*—Howard E. Schain
*Assistant Examiner*—David Lukton
*Attorney, Agent, or Firm*—Carol A. Stratford; Peter J. Dehlinger

[57] ABSTRACT

A method and compositions for reducing neuronal damage related to an ischemic condition in a mammalian subject are described. The method includes administration of a voltage-gated calcium channel-blocking compound to the subject, 4–24 hours after the onset of the ischemic condition. Such a calcium channel blocking compound is effective to block norepinephrine release in mammalian CNS neuronal cells and is characterized by specific, high affinity binding to omega-conotoxin MVIIA binding sites. Also disclosed are novel peptide structures useful in the treatment method of the invention.

5 Claims, 18 Drawing Sheets

OTHER PUBLICATIONS

Sher, E., et al., "Physiopathology of neuronal voltage–operated calcium channels," *FASEB J.* 5:2677–2683 (1991).

Tateishi, A., et al., "Nimodipine Does Not Improve Neurologic Outcome After 14 Minutes of Cardiac Arrest in Cats," *Stroke* 20:1044–1050 (1989).

Wauquier A., et al., "Cerebral Resuscitation: Pathophysiology and Therapy," *Neurosci. Biobehav. Rev.* 11:287–306 (1987).

Widmann, R., et al., "[$^{14}$C]Leucine Incorporation into Brain Proteins in Gerbils After Transient Ischemia: Relationship to Selective Vulnerability of Hippocampus," *J. Neurochem.* 56(3):789–796 (1991).

MVIIA/
SNX-111          C  K  G  K  G  A  K  C  S  R  L  M  Y  D  C  C  T  G  S  C  -  R  -  S  G  K  -  C

MVIIB/
SNX-159          C  K  G  K  G  A  S  C  H  R  T  S  Y  D  C  C  T  G  S  C  N  R  -  -  -  G  K  -  -  C

GVIA/
SNX-124          C  K  S  X  G  S  S  C  S  X  T  S  Y  N  C  C  R  -  S  C  N  X  Y  T  -  K  R  C  -  -  Y

GVIIB/
SNX-178          C  K  S  X  G  T  X  C  S  R  G  M  R  D  C  C  T  -  S  C  L  L  Y  S  N  K  -  C  R  R  Y

RVIA/
SNX-182          C  K  P  X  G  S  X  C  R  V  S  S  Y  N  C  C  S  -  S  C  K  S  Y  -  N  K  K  C  G
```

|  | 1 | 5 | 10 | 15 | 20 | 25 | 30 |
|---|---|---|---|---|---|---|---|
| SVIA/SNX-157 | C R S S G S X C G V T S I - C C - G R C - - Y R G K - C T |
| TVIA/SNX-185 | C L S X G S S C S X T S Y N C C R - S C N X Y S - R K C R |
| SVIB/SNX-183 | C K L K G Q S C R K T S Y D C C S G S C G R - S G K - C |

Fig. 1 (con't)

Fig. 2

|  | 1 | | | | 5 | | | | | 10 | | | | | 15 | | | | | 20 | | | | | 25 | |
|---|---|---|---|---|---|---|---|---|---|---|---|---|---|---|---|---|---|---|---|---|---|---|---|---|---|---|
| MVIIA (SNX-111) | C | K | G | K | G | A | K | C | S | R | L | M | Y | D | C | C | T | G | S | C | R | S | G | K | C | -NH$_2$ |
| SNX-190 | – | – | – | – | A | – | – | – | – | – | – | – | – | – | – | – | – | – | – | – | – | – | – | – | – | NH$_2$ |
| SNX-191 | – | A | – | – | – | – | – | – | – | – | – | – | – | – | – | – | – | – | – | – | – | – | – | – | – | NH$_2$ |
| SNX-193 | – | – | – | – | – | – | – | – | – | – | – | – | – | – | – | – | – | – | – | – | – | – | – | – | – | G-OH |
| SNX-194 | – | – | – | – | – | – | – | – | – | – | – | Nle- | – | – | – | – | – | – | – | – | – | – | – | – | – | NH$_2$ |
| SNX-195 | – | – | – | – | – | – | – | – | – | – | – | – | – | – | – | – | – | – | – | – | – | – | – | A | – | NH$_2$ |
| SNX-196 | N- | – | – | – | – | – | – | – | – | – | – | – | – | – | – | – | – | – | – | – | – | – | – | – | – | G-OH |
| SNX-197 | NS- | – | – | – | – | – | – | – | – | – | – | – | – | – | – | – | – | – | – | – | – | – | – | – | – | NH$_2$ |
| SNX-198 | – | – | – | – | – | – | – | – | – | – | – | – | – | – | – | – | – | – | – | – | A | – | – | – | – | NH$_2$ |
| SNX-200 | – | – | – | – | – | – | A | – | – | – | – | – | – | – | – | – | – | – | – | – | – | – | – | – | – | NH$_2$ |
| SNX-201 | – | – | – | – | – | – | – | – | – | R | K | T | S | – | – | – | – | – | – | – | – | – | – | – | – | NH$_2$ |

```
SVIB        C L K G Q S C R K T S Y D C C S G S C G R S G K C NH₂
(SNX-183)   └─────────┬───────────┘ │ └───────────────────┘
                     └──────────────┘

SNX-202     - - - - - - - - - - - - - - - - - S R L M - - - NH₂

TVIA        C L S X G S S C S X T S Y N C C R S C N X Y S R K C R NH₂
(SNX-185)   └─────────┬───────────┘ │ └─────────────────────┘
                     └──────────────┘

SNX-207     - - - - - - - - - - - - - - - - - - R L M - - - - NH₂
```

Fig. 2 (con't)

MAMMALIAN

200

116

97

- + - +

```
             1         5          10          15          20          25         30
I.
MVIIA        C K G K G A K C S R  L M Y D C  C T G S C  - R - S G  K - C - - -
MVIIB        C K G K G A S C H R  T S Y D C  C T G S C  N R - G K  C - - - - -

II.
GVIA         C K S X G S S C S X  T S Y N C  C R - S C  N X Y T -  K R C - - Y
TVIA         C L S X G S S C S X  T S Y N C  C R - S C  N X Y S R  K - C - - -
SNX-207      C L S X G S S C S R  L M Y N C  C R - S C  N X Y S R  K - C - - -

III.
RVIA         C K P X G S X C R V  S S Y N C  C S - S C  K S Y - N  K - C G - Y
SVIA         C R S S G S X C G V  T S H - C  C - G R C  - G R - Y  R G C T R R
SVIB         C K L K G Q S C R K  T S Y D C  C S G S C  G R - S G  K - C - - -
GVIIA        C K S X G T X C S R  G M R D C  C T - S C  L L Y S N  K - C - R R
SNX-218      C K S T G S S C S R  L M Y N C  C R - S C  N T Y S R  K - C - - Y
```

Fig. 14

DELAYED TREATMENT METHOD OF REDUCING ISCHEMIA-RELATED NEURONAL DAMAGE

This application is a continuation-in-part of application Ser. No. 561,766 filed Aug. 2, 1990, now U.S. Pat. No. 5,189,020 which is in turn a continuation-in-part of application Ser. No. 440,094 filed Nov. 22, 1989, now U.S. Pat. No. 5,051,403.

FIELD OF THE INVENTION

The present invention relates to a method of reducing neuronal damage associated with an ischemic condition, such as stroke.

REFERENCES

Ahmad, S. and Miljanich, G.P., Brain Research, 247–256 (1988).

Bennett, J. P., et al., Neurotransmitter Receptor Binding, pp. 61–89, Raven Press, NY (1983).

Bielenberg, G. W. et al. (1990) Stroke 21: IV90–IV92.

Buchan, A. and Pulsinelli, W. A. (1990) J. Neurosci. 311–316.

Dirnagl, U. et al. (1990) Brain Res. 527: 62–68. Gill, R. et al. (1988) Neuroscience 5: 847–855.

Gray, W., Olivera, B., and Cruz, L. (1988), Annual Review of Biochemistry 57:665–700.

Hartley, D. and Choi, D. (1989), The Journal of Pharmacology and Experimental Therapeutics 250:752–758.

Jacewicz, M. et al. (1990) J. Cereb. Blood Flow Metab. 10: 89–96.

Kaplan B. et al. (1991) Stroke 22: 1032–1039.

Kirino, T., (1982) Brain Research, 239:57–69.

McCleskey, E. W. et al., Proc. Natl. Acad. Sci. USA 84:4327–31 (1987).

Nedergaard, M. (1987) Acta Neuropathol (Berl.) 73: 267–274.

Nowycky, M. C., Fox, A. P., and Tsien, R. W., Nature (London), 316:440–443 (1985).

Pulsinelli, W. A., et al, (1979), Stroke, 10:267–272.

Pulsinelli, W. A., et al, (1982) Ann. Neurol. 11: 491–498.

Olivera, B., Mcintosh, J., Cruz, L., Luque, F., and Gray, W. 1984), Biochemistry 23:5087–5090.

Rivier, J., et al., J. Biol. Chem. 262:1194–1198.

Sano, K., et al (1987), Eur J Pharmacol, 141:235–241.

Sher, E. et al. (1991) FASEB J. 5: 2677–2683.

Tateishi, A., Fleischer, J., Drumond, J., Scheller, M., Zornow, M., Grafe, M., and Schapiro, H. (1989), Stroke 20:1044–1050.

Vibulsreth, S., Dietrich, W., Busto, R., and Ginsberg, M. (1987), Stroke 18:210–216.

Wauquier, A., Edmonds, H., Clincke, G. (1987), Neuroscience and Biobehavioral Reviews 11:287–306.

BACKGROUND OF THE INVENTION

Ischemic damage to the central nervous system (CNS) may result from either global or focal ischemic conditions. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, or brain tumors.

Both global and focal ischemic conditions have the potential for producing widespread neuronal damage, even if the global ischemic condition is transient or the focal condition affects a very limited area.

Although these conditions appear to have similar underlying biochemical sequelae, the time scale over which they produce their respective damage may vary. Thus, in global ischemia, in which cessation of blood flow is transient, though some permanent neuronal injury may occur in the initial minutes following cessation of blood flow to the brain, much of the damage appears several days following the ischemic event. Moreover, certain regions of the brain are selectively vulnerable to the effects of global ischemia (Kirino, Pulsinelli (1982)). Secondary consequences of reperfusion of the tissue, such as the release of vasoactive products by damaged endothelium, and the release of cytotoxic products (free radicals, leukotrienes, etc.) by damaged tissues have been hypothesized to underlie the observed delay in neuronal damage.

Focal ischemia, on the other hand, may be of limited or prolonged duration. In the case of prolonged focal ischemia, as caused by lodgement of a thromboembolus in a cerebral blood vessel, reduction of blood flow to a defined, focal region may be followed by reperfusion to part of the ischemic region, via collateral circulatory pathways. Ischemic cell death following focal ischemia has been reported to be complete 24 hours after the primary ischemic event (Nedergaard, 1987).

Several drug strategies have been proposed for treatment of stroke and other neuronal conditions related to ischemia, and these have been reviewed in recent articles (e.g., Greenberg, Wauquier). Anti-coagulants, such as heparin, have been examined, but with mixed results. Similarly, antivasoconstriction agents, such as flunarizine, excitatory neurotransmitter antagonists, such as MK-801 and AP7, and anti-edemic compounds have shown mixed results, with no clear benefits to outweigh a variety of side effects, including neurotoxicity or increased susceptibility to infection.

Two general classes of vasodilators have been studied for possible treatment of neuronal ischemic damage. Non-specific vasodilators, including papaverine, prostacyclin, pentoxifylline, and nitroprusside failed to demonstrate any clear benefit in reducing ischemic damage. A second general class of vasodilators includes a variety of calcium-antagonist vasodilator drugs. Verapamil and related compounds which prevent calcium entry into smooth and striated muscle appear to be effective only at high drug concentrations, where serious cardiotoxicity effects may ensue. Dihydropyridines, such as nimodipine, have produced mixed results— some neurological improvement may be seen, but increased cerebral edema has also been observed. Benzothiazepines, as exemplified by diltiazem, have shown moderate protective effects, but these drugs also appear to cause undesired side effects.

In general, the drugs mentioned above have been administered prior to or within a few hours of the period of experimental ischemic insult. In clinical practice, particularly in the treatment of stroke, treatment is generally not feasible until well after the ischemic insult. In those studies in which post-ischemia treatment has been given, the treatment paradigms have generally included treatment commencing before the ischemic event and continuing over an extended period of time, such as continuous administration of nimodipine from one hour before until 24 hours following ischemia (Jacewicz), or repeated doses administered before as well as after the ischemic event (Dirnagl, 1990; Bielenberg, 1990). In one study, the NMDA antagonist MK-801 was administered to Mongolian gerbils 24 hours post-ischemia, and neuroprotection was observed (Gill et al., 1988); however, the effects of this compound have subsequently been shown to be a consequence of postischemic hypothermia rather than a direct action on NMDA receptors in this animal model (Buchan and Pulsinelli, 1990).

In summary, drugs which have been proposed to date for the treatment of stroke and other ischemic-related conditions of the brain are either (i) relatively ineffective, (ii) effective only at dosage levels where undesired side effects are observed, and/or (iii) effective only when administered prior to or shortly after the ischemic insult.

In the parent U.S. Pat. No. 5,051,403 and U.S. Pat. No. 5,189,020, filed Nov. 22, 1989, and Aug. 2, 1990, respectively, the applicants have disclosed that omega-conotoxin peptides and related peptides which exhibit binding and N- or omega-type calcium channel inhibitory properties similar to those of omega-conotoxin peptides are useful in reducing neuronal damage related to ischemic conditions. In the above-referenced applications, both of which are incorporated herein by reference, experiments attesting to the efficacy of these compounds were conducted in accordance with standard experimental paradigms for examining neuroprotection. That is, test compounds were administered at the time of or up to 1 hour following the experimentally induced occlusion which caused the ischemic event. In the current application, the applicants show that reduction of neuronal damage can be enhanced when the N-channel blocking compound is administered between 4–24 hours following ischemia, relative to immediate post-ischemia drug administration.

SUMMARY OF THE INVENTION

It is therefore a general object of the invention to provide a method for reducing neuronal damage related to an ischemic injury in the brain.

Another object of the invention is to provide novel peptides for treating such neuronal injury.

In the method of the invention a patient is administered a pharmaceutically acceptable amount of a voltage-gated calcium channel-inhibitory compound, 4–24 hours following the onset of the ischemic condition. The inhibitory compound is characterized by the ability to inhibit voltage-gated calcium channels, as evidenced by the compound's ability to (a) inhibit neurotransmitter release selectively in neuronal tissue, and (b) bind to omega-conotoxin binding sites present in neuronal tissue. One general class of compounds useful in the method of the invention includes omega-conotoxin peptides. Preferred omega-conotoxins include omega-conotoxins MVIIA, GVIA, TVIA, and SNX-207.

In a preferred embodiment of the invention, the compound's ability to bind to omega-conotoxin binding sites is characterized by competitive displacement of omega-conotoxin MVIIA from neuronal membranes and the activity for inhibition of neurotransmitter release is characterized by inhibition of norepinephrine release from mammalian central nervous system neuronal cells. In yet another preferred embodiment, the binding and neurotransmitter release inhibitory activities of the compound are within the range of such activities for omega-conotoxins MVIIA (SNX-111), GVIA (SNX-124), SNX-207 and TVIA (SNX-185).

In still another preferred embodiment, the activity for binding is characterized by the ratio of binding constants of the compound for the central nervous system omega-conotoxin MVIIA (SNX-111) binding site and for the central nervous system SVIB (SNX-183) binding site.

The invention further includes an omega conotoxin peptide having the form: SEQ ID NO:22–$X_1$–SEQ ID NO: 23–$X_2$–SEQ ID NO: 25–$X_3X_4$–SEQ ID NO: 24–$X_5$–SEQ ID NO:25–$X_6$–SEQ. I.D. No. 26–t, where $X_1$=K or S; $X_2$=S or H; $X_3$=L or T; $X_4$=M or S; $X_5$=N or a deletion; $X_6$=S or deletion, and t=a carboxy or amidated carboxyterminal group, excluding the peptides in which $X_1$=K, $X_2$=S, $X_3$=L, $X_4$=M, $X_5$=deletion, and $X_6$=S; and $X_1$=S, $X_2$=H, $X_3$=T, $X_4$=T, $X_5$=N, and $X_6$=deletion.

Another preferred omega-conotoxin peptide has the form: SEQ ID NO: 23–$X_1$–SEQ ID NO: 27–$X_2X_3X_4$–SEQ ID NO: 28–$X_5X_6$ $X_7$–SEQ ID NO: 23–$X_8$–t, where $X_1$=K or L; $X_2$=X or R; $X_3$=T or L; $X_4$=S or M; $X_5$=T or S; $X_6$=K or R; $X_7$=R or K; and $X_8$=Y or R, and t=a carboxy or amidated carboxyterminal group, excluding the peptides in which $X_1$=K, $X_2$=X, $X_3$=T, $X_4$=S, $X_5$=T, $X_6$=K, $X_7$=R, and $X_8$=Y; and $X_1$=L, $X_2$=X, $X_3$=T, $X_4$=S, $X_5$=S, $X_6$=R, $X_7$=K, and $X_8$=R. A preferred peptide has the structure SEQ ID NO:21–t, wherein t=a carboxy or amidated carboxyterminal group.

Still another object of the invention is to provide a pharmaceutical composition for reducing neuronal damage related to an ischemic condition, when the composition is administered to the subject 4–24 hours following the onset of the ischemic condition. The composition generally includes a peptide which selectively inhibits voltage-gated calcium channels, as evidenced by the peptide's ability to selectively inhibit neurotransmitter release in neuronal tissue and to bind to omega-conotoxin binding sites present in neuronal tissue. The composition also includes a sterile injectable medium in which the compound is carried.

In a preferred embodiment, the pharmaceutical composition includes an omega-conotoxin peptide. In yet another preferred embodiment, the pharmaceutical composition includes omega conotoxins MVIIA, GVIA, TVIA, and SNX-207. In still a further embodiment of the invention, the pharmaceutical composition is a peptide having the form SEQ ID NO: 23–$X_1$–SEQ ID NO: 27–$X_2X_3X_4$–SEQ ID NO: 28–$X_5X_6X_7$–SEQ ID NO: 23–$X_8$–t, where $X_1$=K or L; $X_2$=X or R; $X_3$=T or L; $X_4$=S or M; $X_5$=T or S; $X_6$=K or R; $X_6$=R or K; and $X_8$=Y or R, and t=a carboxy or amidated carboxyterminal group.

These and other objects and features of the invention will become more apparent when the following detailed description of the invention is read in conjunction with the accompanying drawings.

BRIEF DESCRIPTION OF THE FIGURES

FIG. 1 shows primary sequences of several natural OCT peptides, MVIIA/SNX-111 (SEQ ID NO: 01), MVIIB/SNX-159 (SEQ ID NO: 02), GVIA/SNX-124 (SEQ ID NO: 03), GVIIA/SNX-178 (SEQ ID NO: 04), RVIA/SNX-182 (SEQ ID NO: 05), SVIA/SNX-157 (SEQ ID NO: 06), TVIA/SNX-185 (SEQ ID NO: 07), and SVIB/SNX-183 (SEQ ID NO: 08);

FIG. 2 shows several analog OCT peptides SNX-190 (SEQ ID NO: 09), SNX-191 (SEQ ID NO: 10), SNX-193 (SEQ ID NO: 11), SNX-194 (SEQ ID NO: 12), SNX-195 (SEQ ID NO: 13), SNX-196 (SEQ ID NO: 14), SNX-197 (SEQ ID NO: 15), SNX-198 (SEQ ID NO: 16), SNX-200 (SEQ ID NO: 17), SNX-201 (SEQ ID NO: 18), SNX-202

Figure 3A:
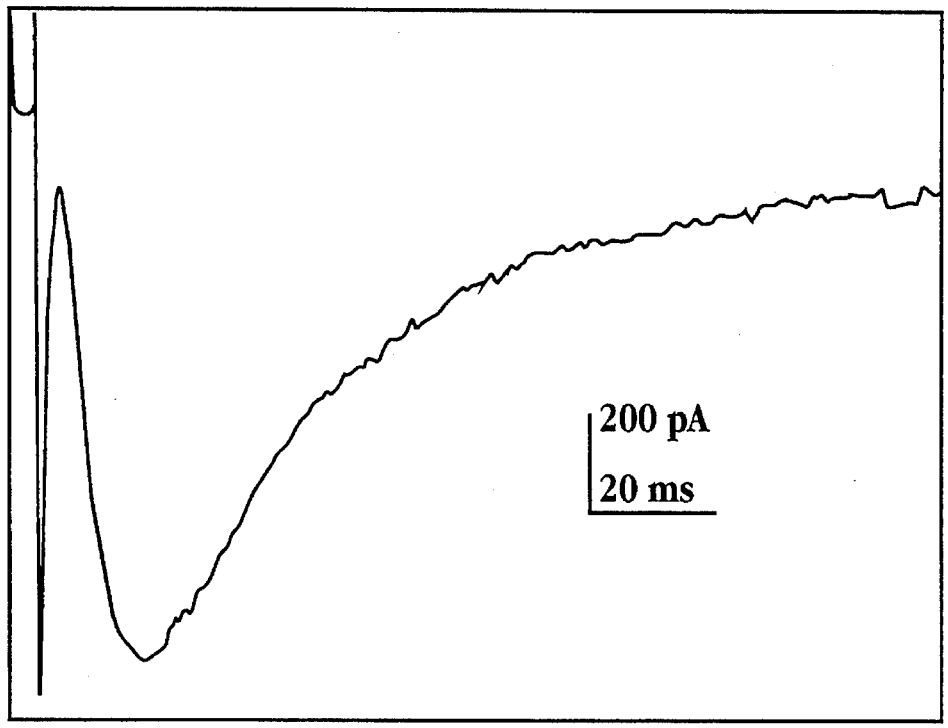
Figure 3B:
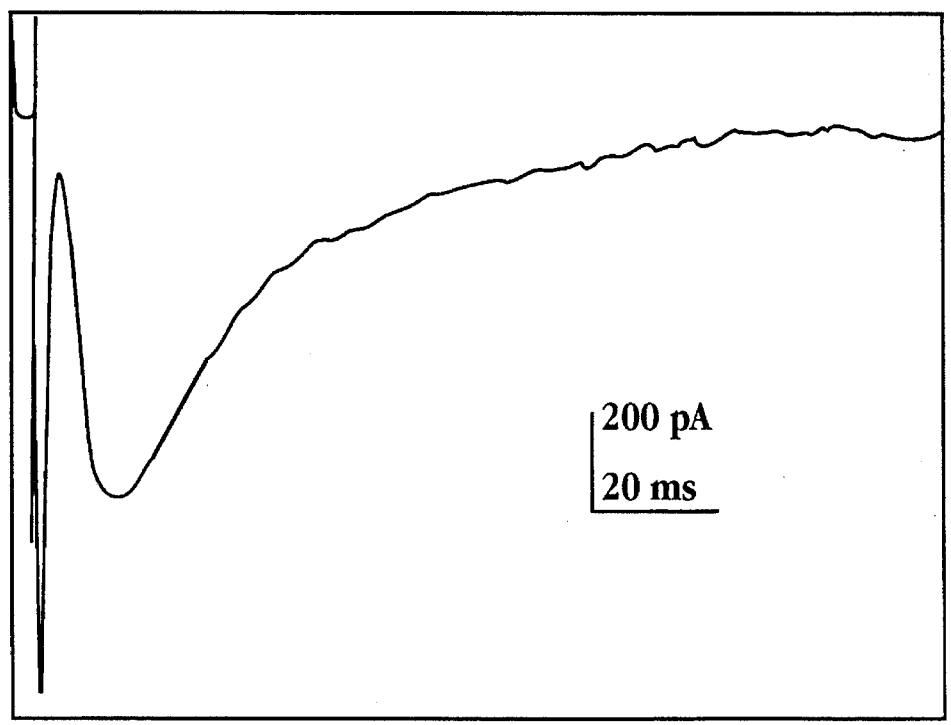
Figure 3C:
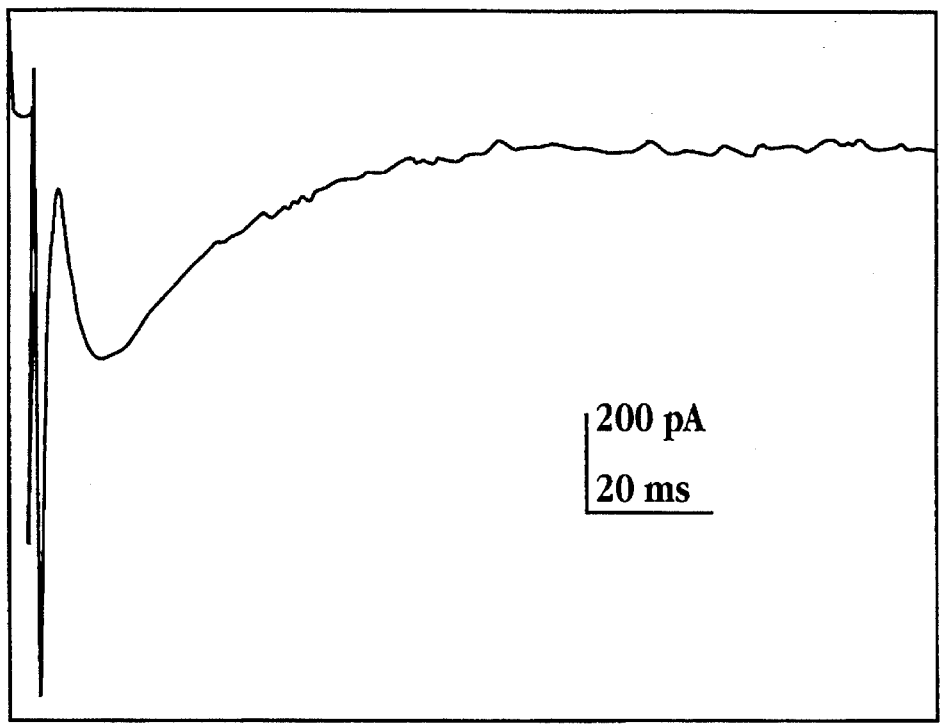
Figure 3D:
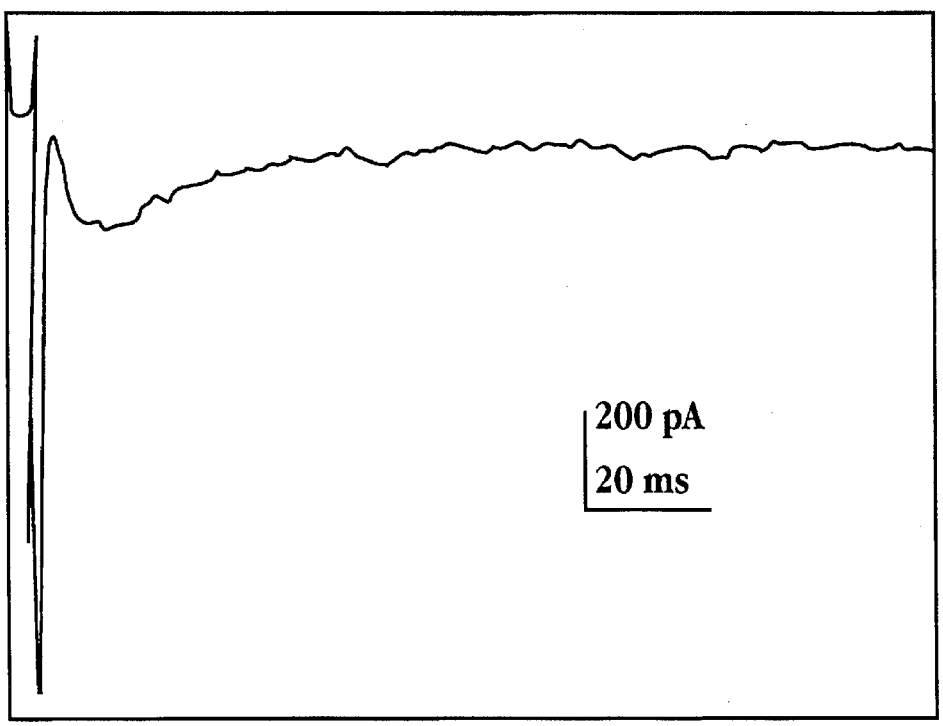
Figure 3E:
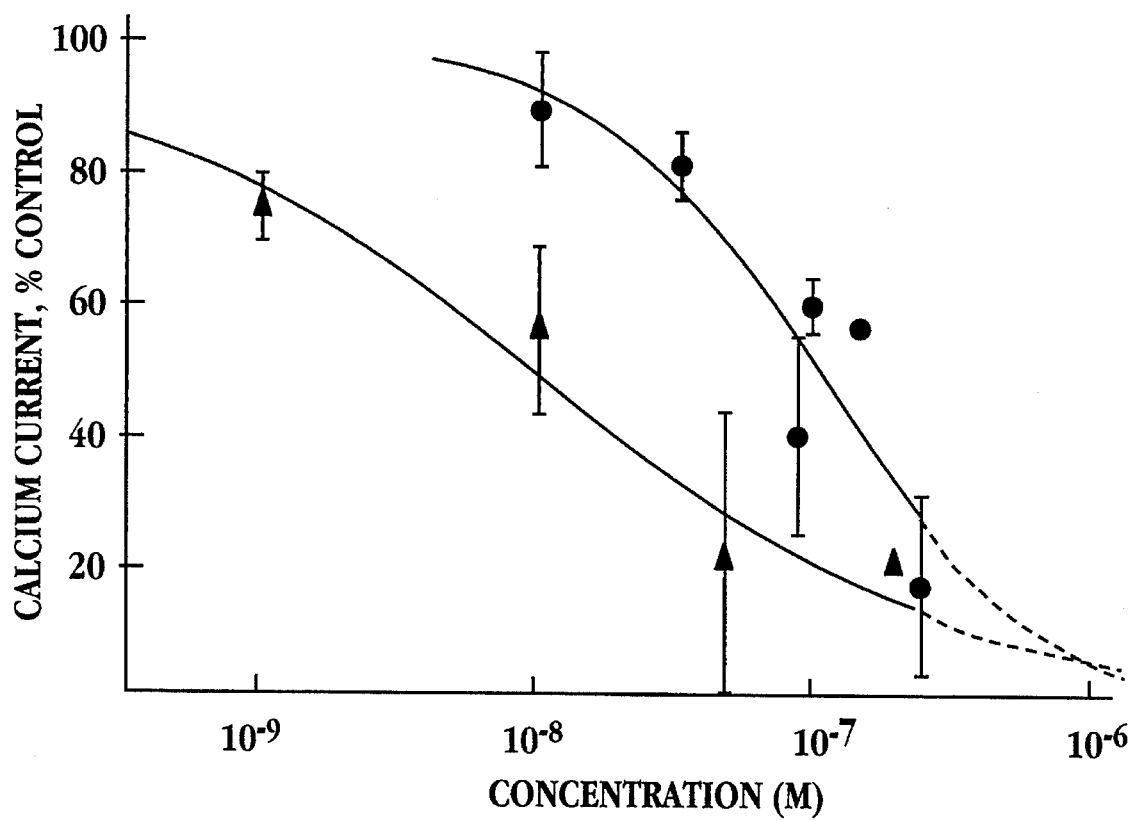
Figure 4A:
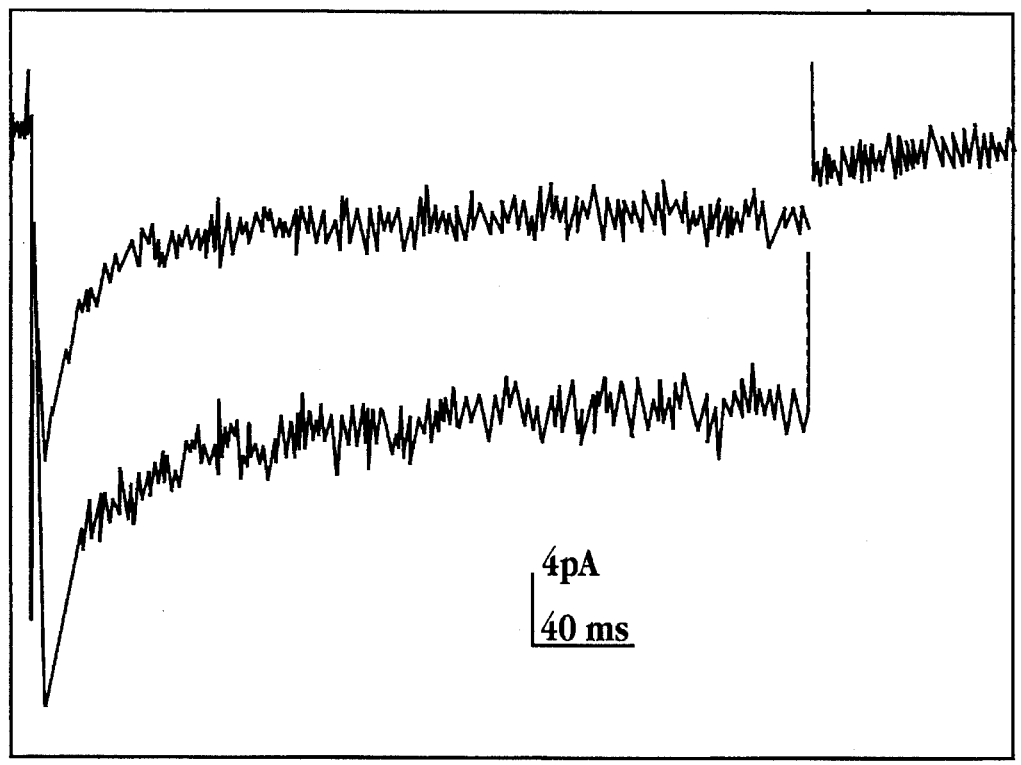
Figure 4B:
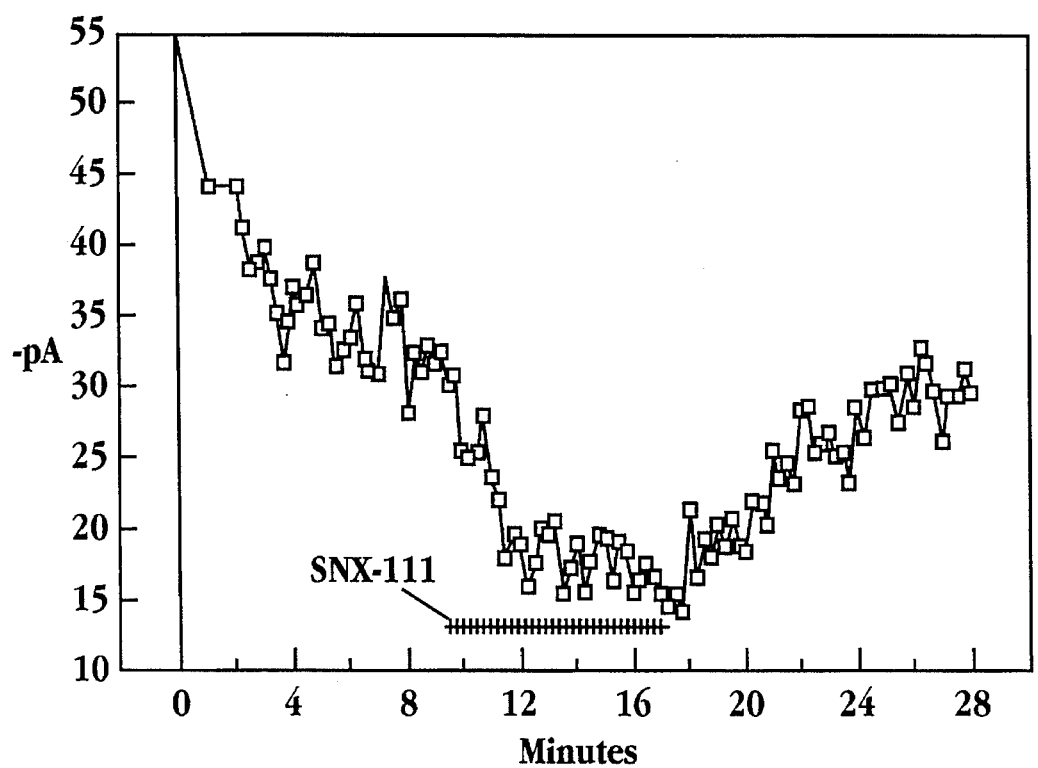
Figure 4C:
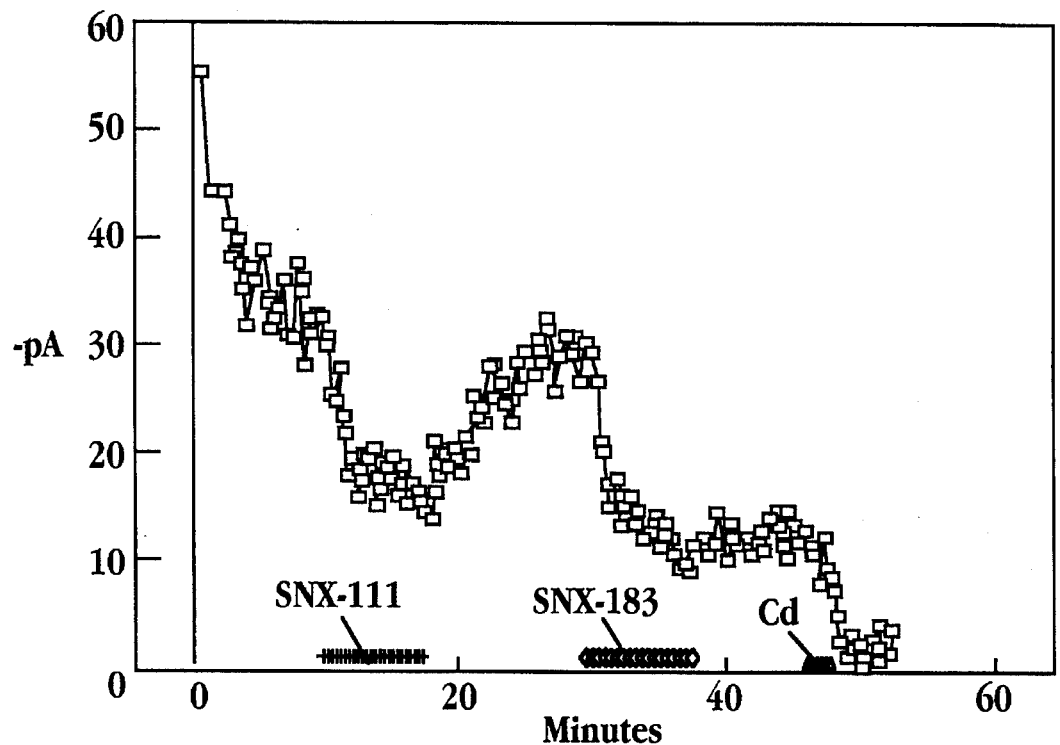
Figure 5:
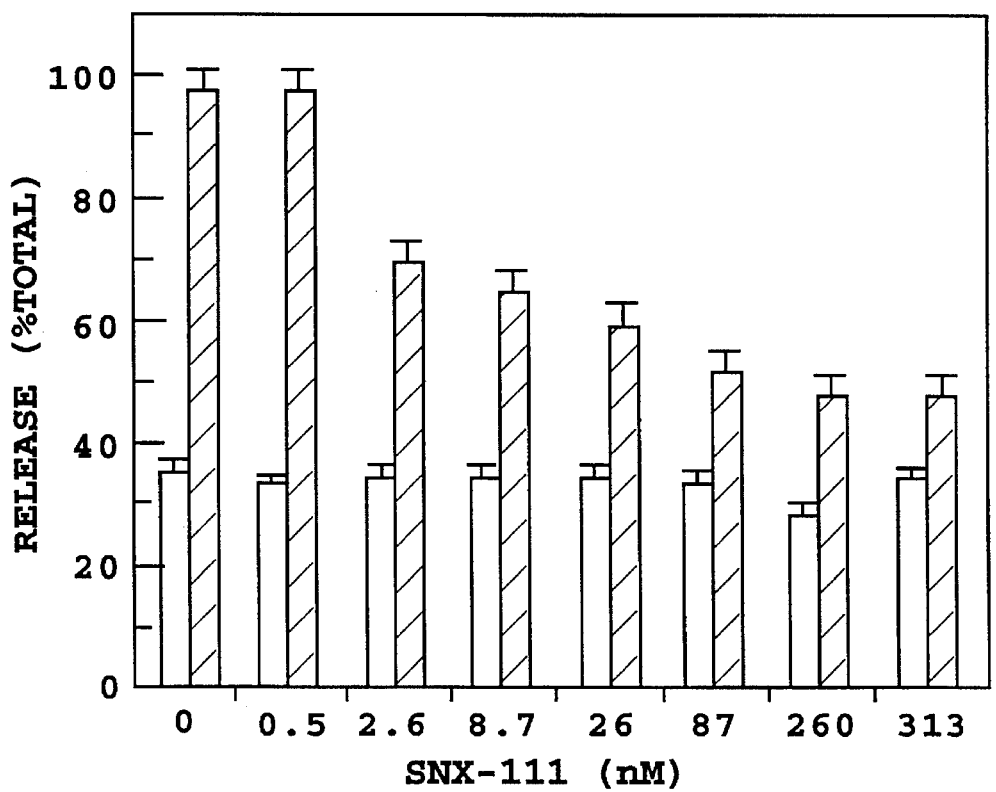
Figure 6A:
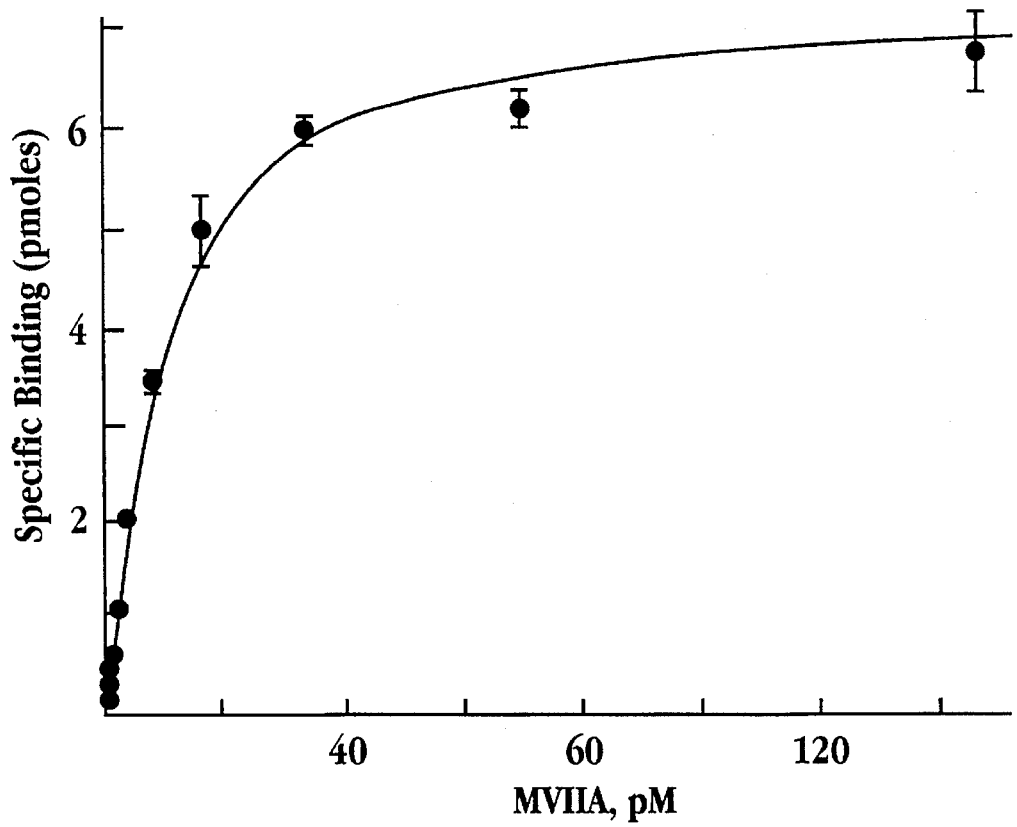
Figure 6B:
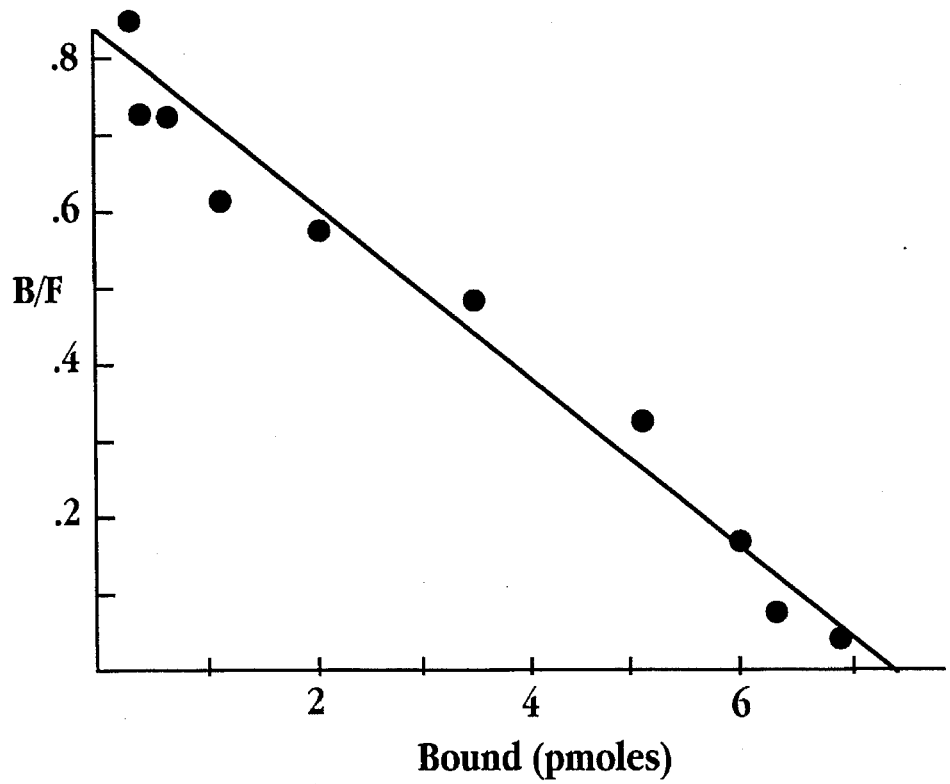
Figure 7:
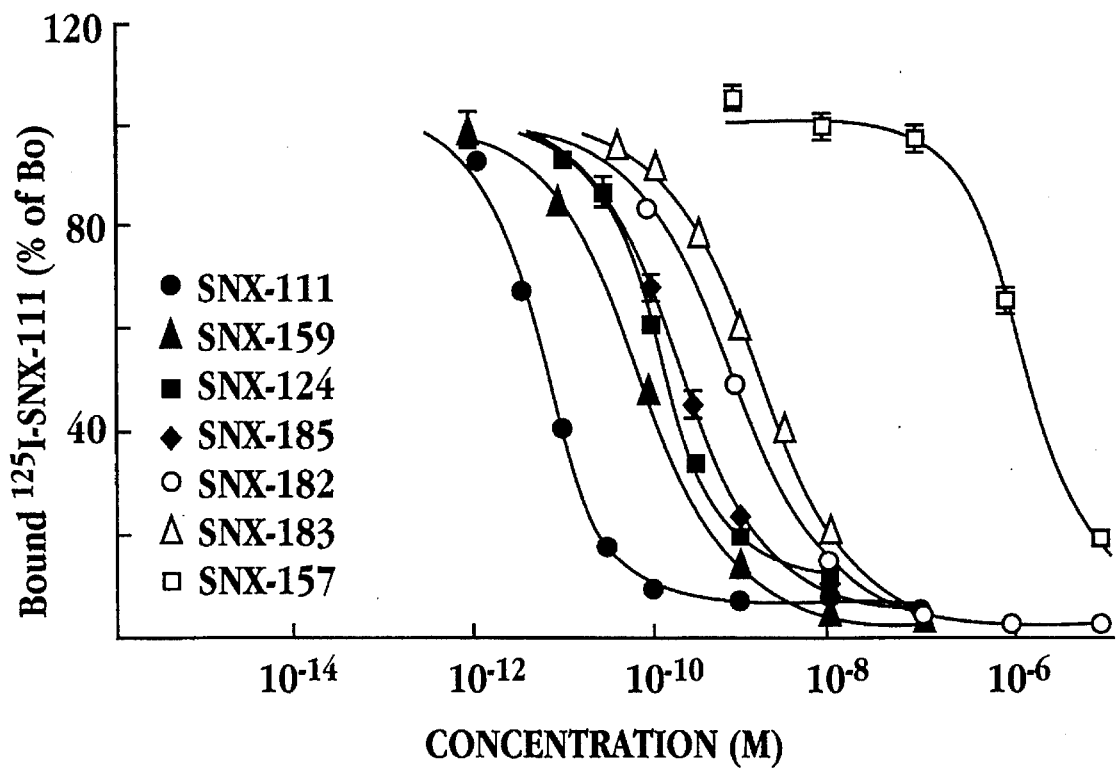
Figure 9:
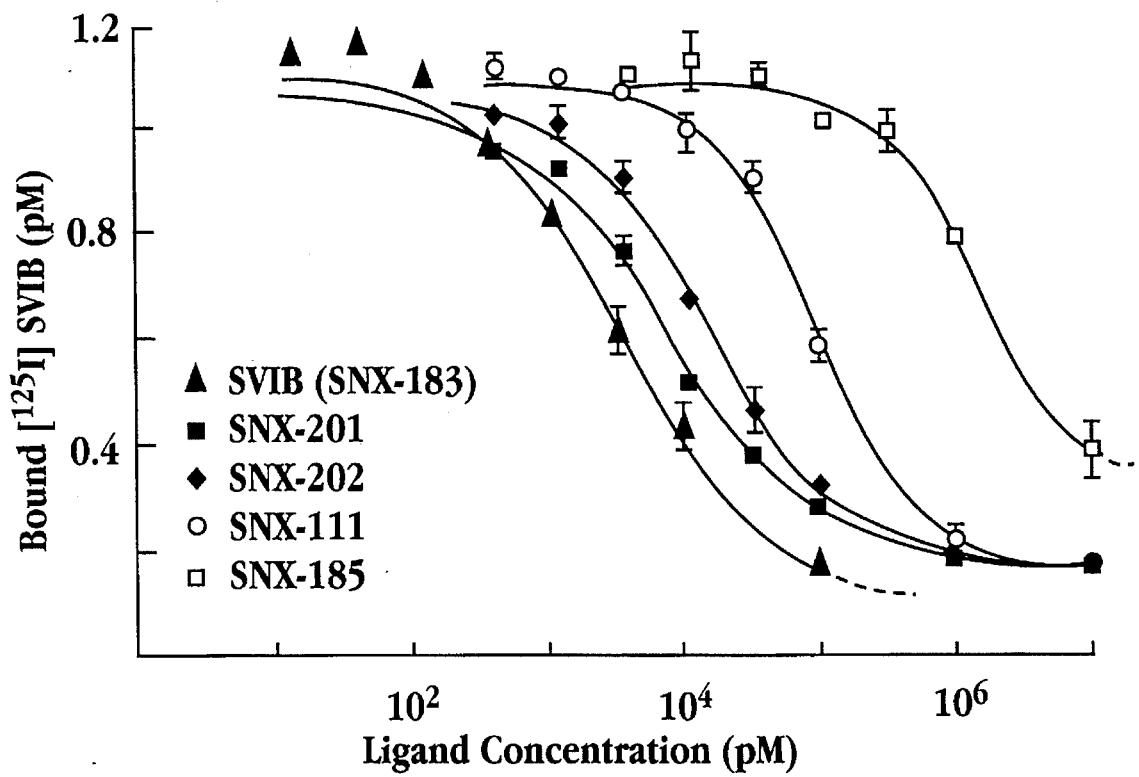
Figure 8:
Figure 10A:
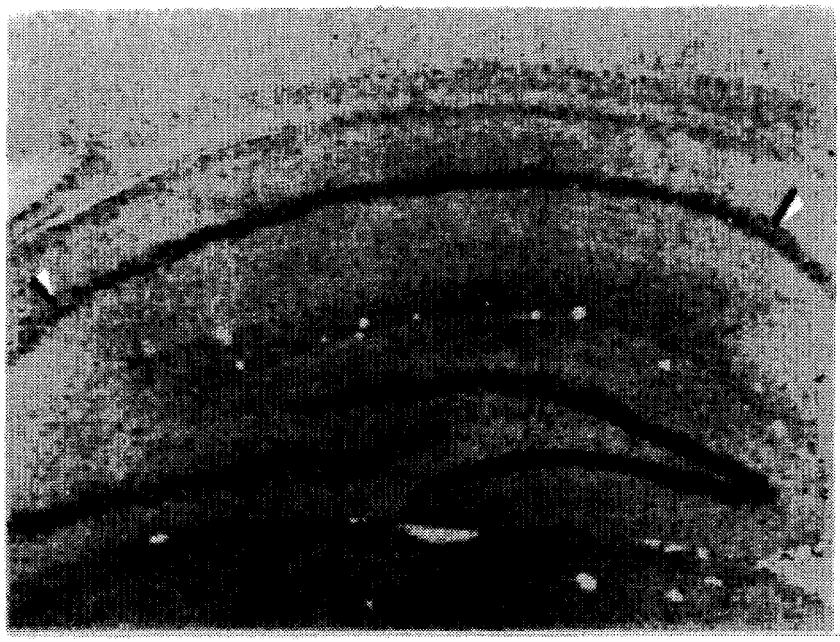
Figure 10B:
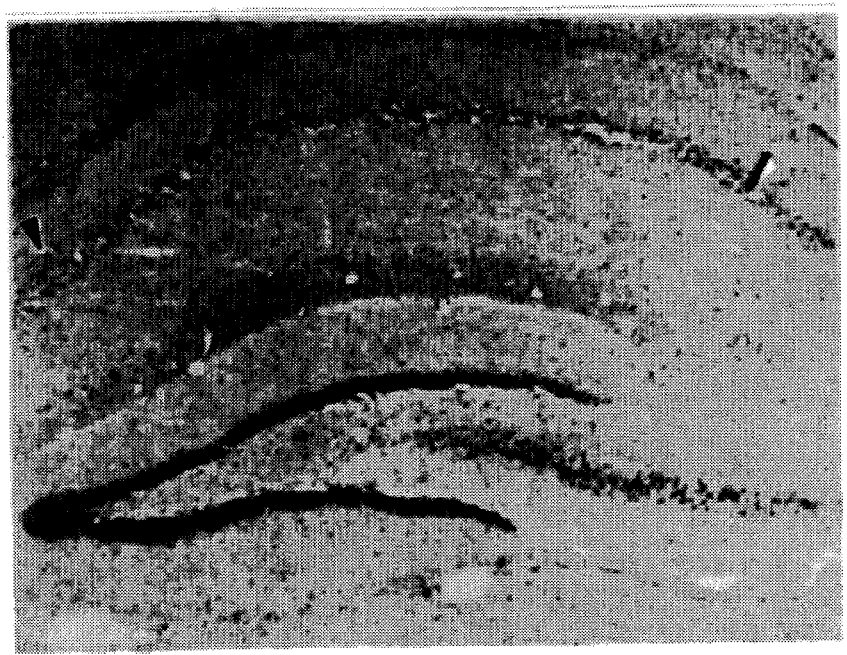
Figure 12:
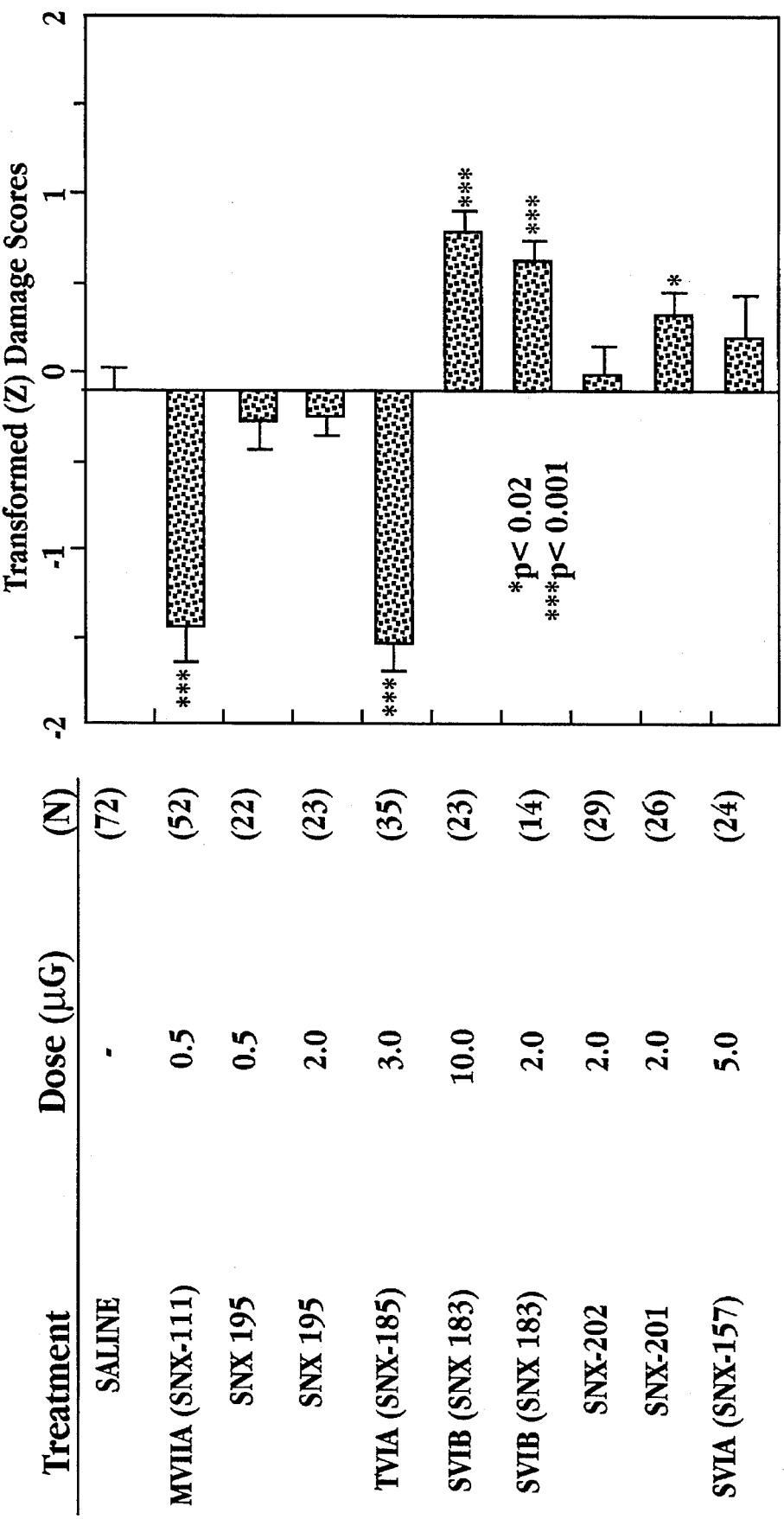
Figure 13:
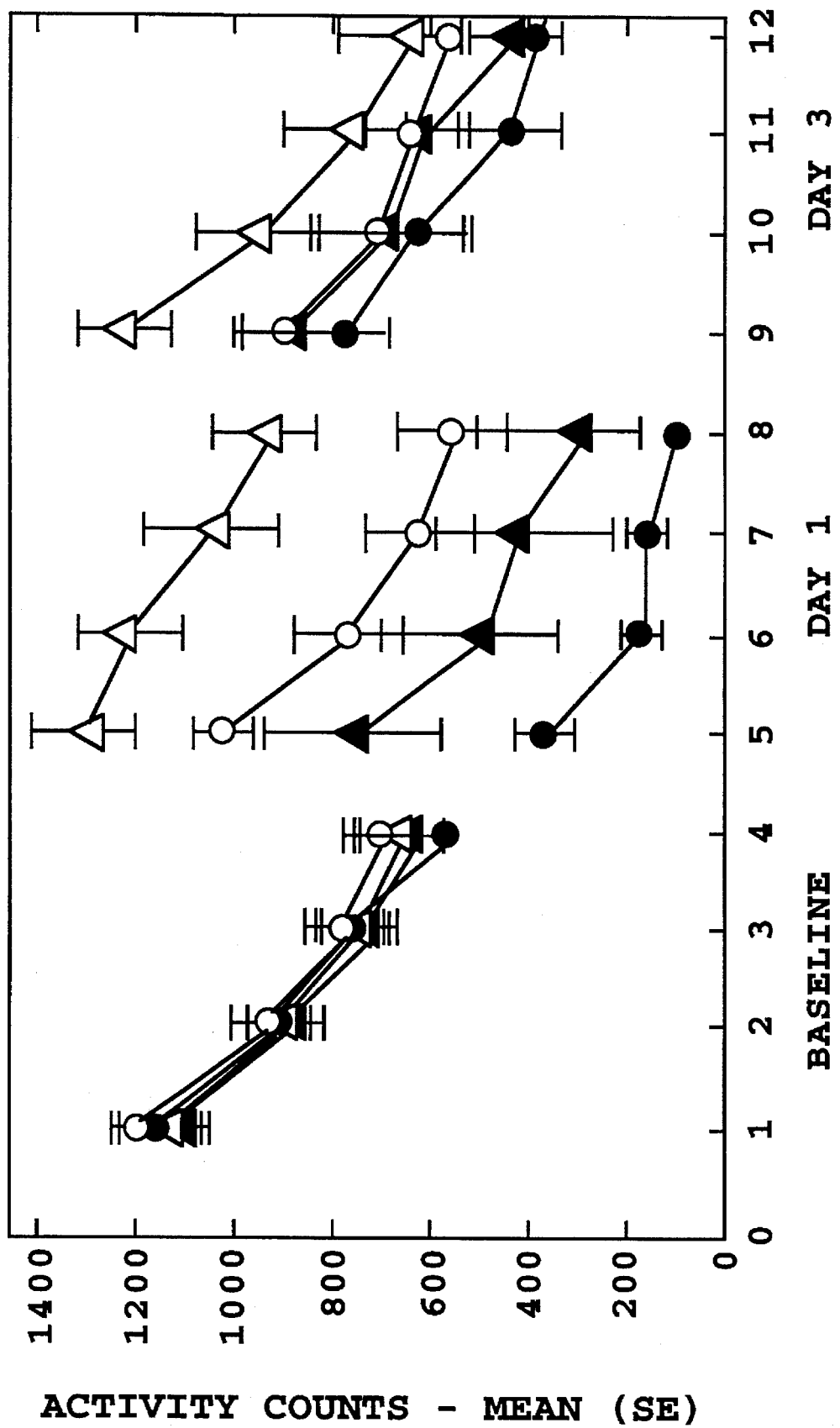

(SEQ ID NO: 19), SNX-207 (SEQ ID NO: 20), and their relationships to SNX-111 (SEQ ID NO: 01), SNX-185 (SEQ ID NO: 07) or SNX-183 (SEQ ID NO: 08);

FIGS. 3A–3D show voltage-gated calcium current traces induced by a voltage step from −100 or −80 mV to −20 mV in untreated N1E-115 neuroblastoma cells (3A) and in neuroblastoma cells exposed to increasing concentrations of OCT MVIIA (SNX-111) (3B–3D);

FIG. 3E plots the percent inhibition of peak inward calcium currents in neuroblastoma cells as a function of OCT MVIIA (SNX-111) (solid triangles) and OCT GVIA (SNX-124)(solid circles);

FIG. 4A shows voltage-gated calcium current traces induced by a voltage step from −70 to −20 mV in human neuroblastoma cells (IMR-32) in the absence (lower trace) and presence (upper tracing) of 150 nM SNX-111;

FIGS. 4B and 4C show plots of absolute values of peak inward current measured every 15 seconds in IMR-32 cells, elicited by pulses from −70 to 0 or −10 mV, versus time, where addition of compounds SNX-111 (4B) or SNX-111, SNX-183 (4C), and cadmium to the bathing medium are indicated by hatch marks just above the ordinate;

FIG. 5 shows the inhibition of norepinephrine release from neuronal cells as a function of OCT MVIIA (SNX-111) concentration (solid bars are potassium stimulated and open bars are basal values);

FIGS. 6A and 6B are a binding curve showing the amount of OCT MVIIA (SNX-111) bound to rat synaptosomal membranes, as a function of OCT MVIIA (SNX-111) concentration (6A), and the same data plotted as a Scatchard plot (6B);

FIG. 7 shows computer-fit competitive binding curves for OCT peptide binding to the OCT MVIIA (SNX-111) binding site in rat brain synaptosomes;

FIG. 8 shows an SDS-PAGE autoradiogram of rat synaptosomal membranes having covalently bound radiolabeled OCT MVIIA (SNX-111)(lanes a and b) or covalently bound OCT GVIA (SNX-124)(lanes c and d) added to the membranes in the presence (lanes b and d) or absence (lanes a and c) of non-radiolabeled OCT;

FIG. 9 shows computer-fit competitive binding displacement curves for OCT peptide binding to OCT SVIB (SNX-183) binding sites in rat brain synaptosomes;

FIG. 10A–10B are low-power micrographs of gerbil hippocampus CA1 region in animals after ischemia, and infusion of OCT MVIIA (SNX-111) (10A) or after ischemia and infusion of drug vehicle (10B);

FIGS. 11A–11D are higher power micrographs of cells in the drug-treated ischemic animals (11A, 11C, 11D), in animals receiving vehicle alone (11B), in animals showing complete protection by OCT against ischemic cell damage (11C); and in animals showing partial protection by OCT against ischemic cell damage (11D);

FIG. 12 shows the degree of neuroprotection observed with a variety of OCT peptides in the rat 4-vessel occlusion ischemia model of neuroprotection;

FIG. 13 plots the changes in spontaneous motor activity in animals which were (a) unoccluded and untreated (open circles), (b) unoccluded and treated with MVIIA (SNX-111) peptide (closed circles), (c) occluded but untreated (open triangles), and (d) occluded and treated with MVIIA peptide (closed triangles); and FIG. 14 shows amino acid sequences of active (groups I and II) and inactive (group III) OCT peptides.

DETAILED DESCRIPTION OF THE INVENTION

I. OCT Peptides

Omega-conotoxin (OCT) peptides are peptide toxins produced by marine snails of the genus Conus, and which act as calcium channel blockers (Gray). About 500 species of cone snails in the Conus genus have been identified, and a variety of OCT peptides from several of these species have been isolated. Omega-conotoxin peptides are alternatively referred to as "OCT peptides" or "omega-conopeptides" herein. The primary sequences of eight natural OCT peptides are shown in FIG. 1. Conventional letter initials are used for the amino acid residues, and X represents 4-hydroxyproline, also abbreviated 4Hyp. All of the peptides shown in the figure are amidated at their C-termini.

The peptides shown in FIG. 1 are identified by names which are commonly associated with either the naturally occurring peptide (single letter followed by a Roman numeral followed by a single letter), and by a synthetic designation (SNX-plus numeral). Either or both of these designations will be used interchangeably throughout the specification. For example, the peptide whose sequence is designated MVIIA/SNX-111 will be referred to herein as OCT MVIIA, or alternatively, SNX-111, the latter to signify that the compound is synthetic in origin. Synthetic and naturally occurring peptides having the same sequence behave substantially identically in the assays and methods of treatment of the invention. The OCT MVIIA (SNX-111) and OCT GVIA (SNX-124) peptides also have the common names CmTx and CgTx, respectively. All of the OCT peptides have three disulfide linkages connecting cysteine residues 1 and 4, 2 and 5, and 3 and 6, as indicated for the MVIIA peptide in FIG. 2. FIG. 2 shows analogs of natural OCT MVIIA, OCT TVIA, and OCT SVIB peptides which have been synthesized and tested in accordance with the invention. Standard single amino acid code letters are used in the figure; X=hydroxyproline; Nle=norleucine; $NH_2$ group at the C terminus indicates that the peptide is C-terminal amidated; G-OH indicates termination in an unmodified glycine residue.

A. Preparation of OCT Peptides

This section describes the synthesis, by solid phase methods, of several naturally occurring omega conotoxin (OCT) peptides and additional OCT peptides which are used in the present invention.

OCT peptides, such as those shown in FIGS. 1 and 2, can be synthesized by conventional solid phase methods, such as have been described (Olivera). Briefly, N-alpha-protected amino acid anhydrides are prepared in crystallized form and used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1–2 reaction cycles are used for the first twelve residue additions, and 2–3 reaction cycles for the remaining residues.

After completing the growing peptide chains, the protected peptide resin is treated with liquid hydrofluoric acid to deblock and release the peptides from the support. For preparing an amidated peptide, the resin support used in the synthesis is selected to supply a C-terminal amide, after peptide cleavage from the ring.

The three disulfide linkages in the peptides may be formed by air oxidation in the presence of dithiothreitol (DTT) at room temperature or at 4° C. over an extended reaction period. Alternatively, where the correct or desired bridging cannot be achieved by random oxidation, a chemically directed process may be used in which the bridges are formed sequentially, one bridge at a time. The following side-chain protecting groups could be used for each pair of cysteine residues: 4-methylbenzyl, ethylcarbamoyl, and acetamidomethyl. These protecting groups constitute an orthogonal set in which any one kind of protecting group can be removed under conditions that do not affect the other two.

The strategy used in this method involves removing one kind of protecting group from a pair of cysteine residues, followed by oxidation to form the first disulfide bridge. A second kind of protecting group is then removed, again followed by oxidation to form the second bridge. A third bridge, if needed, is formed in like manner.

The peptide can be isolated by an initial separation by gel filtration, to remove peptide dimers and higher molecular weight polymers, and also to remove undesired salts, such as guanidine hydrochloride, used in the oxidation reaction. The partially purified peptide is further purified by preparative HPLC chromatography, and the purity of the peptide confirmed by amino acid composition analysis.

II. In vitro Properties of OCT Peptides

A. Calcium-Channel Antagonist Activity

The neuroprotective compounds of the invention are neuronal-cell calcium channel antagonists, as defined by their ability to inhibit voltage-gated ionic currents in neuronal cells.

Voltage-gated calcium channels are present in neurons, and in cardiac, smooth, and skeletal muscle and other excitable cells, and are known to play a variety of roles in membrane excitability, muscle contraction, and cellular secretion, such as in synaptic transmission (McCleskey). In neuronal cells, voltage-gated calcium channels have been classified by their electrophysiological as well as by their biochemical (binding) properties. Electrophysiologically, these channels can be classified either as Low-voltage-activated (LVA) or High-voltage-activated (HVA). HVA channels are currently known to comprise at least three groups of channels, known as L-, N- and P-type channels (Nowycky, Sher). These channels can be distinguished electrophysiologically as well as biochemically on the basis of their pharmacology and ligand binding properties. Thus, dihydropyridines, diphenylalkylamines and piperidines bind to the alpha$_1$ subunit of the L-type calcium channel and block a proportion of HVA calcium currents in neuronal tissue, which are termed L-type calcium currents.

Omega conotoxins also block a proportion of HVA calcium currents in neuronal tissue, and, in the presence of a maximally inhibitory quantity of dihydropyridine compound, effect substantially inhibition the remaining HVA currents in neuronal cells. These calcium currents are identified as N-type calcium currents, though recently a proposal that such currents be termed "omega" has been presented (Sher). Omega conotoxins bind to a specific population of binding sites. Dihydropyridines and other L-type channel blockers do not displace omega conotoxin binding, nor do omega conotoxins displace binding of ligands to L-channels. Unlike L-type calcium channels, omega channels are found predominantly, although not exclusively, in nervous tissue (Sher).

One suitable system for testing inhibition (blockage) of N-type or omega HVA neuronal calcium channels is an isolated cell system, such as the mouse neuroblastoma cell line, strain N1E115 or the human neuroblastoma cell line IMR32. Membrane currents are conveniently measured with the whole cell configuration of the patch clamp method, according to the procedure detailed in Example 1. Briefly, a voltage clamp protocol was performed in which the cell potential was stepped from the holding potential of about −100 mV to test potentials that ranged from −60 mV to +20 mV, and the cell was held at the holding potential for 5 seconds between pulses.

FIG. 3 shows a typical inward calcium current elicited by a voltage step from −80 mV to −20 mV in the absence of OCT. In this, and most of the recordings shown, barium (Ba) replaced calcium (Ca) as the charge-carrier through the calcium channels in order to increase the signal (McCleskey). According to the procedure described in Example 1, an N1E115 neuroblastoma cell was bathed in saline with sodium replaced by N-methyl-D-glucamine (NMDG), and 10 mM Ba instead of 2 mM Ca. These substitutions reduced the sodium current that would otherwise have contaminated the calcium current record, and increased the calcium current above what it would have been with only 2 mM Ca in the bath. Potassium currents were blocked by tetraethylammonium (TEA) in the bath and cesium (Cs) in the pipet solution.

As seen from FIG. 3, curve A, the calcium current activates quickly (within about 20 ms) and inactivates with a time constant of 30 to 40 ms. The calcium current is measured by the amplitude of the peak inward current elicited by the depolarization peak, and has a measured value of about −1200 pA. The cell in FIG. 3 (curve A) was also exposed to 1 μM nifedipine, a dihydropyridine, which is expected to effectively block L-type calcium channels in the neuroblastoma cells, and no effect on the measured calcium current was observed. The calcium current observed is thus not dihydropyridine-sensitive. The responses of voltage-gated calcium current to increasing concentrations of OCTs MVIIA (SNX-111) and GVIA (SNX-124) are shown in FIG. 3E. The ED$_{50}$ concentration, at which 50% inhibition of calcium current is produced, is determined from the voltage-gated current amplitudes, plotted as a function of OCT peptide concentration. The calculated ED$_{50}$ is about 10 nM for GVIA and 100 nM for MVIIA, indicative of high inhibitory peptide activity. The ED$_{50}$ concentration for these and OCT peptides SVIA (SNX-157) and SVIB (SNX-183) are given in Table 1 below. The two compounds with relatively low IC$_{50}$ values (below 1 μM) are both active as neuroprotective agents, as will be seen in Section III below, whereas the OCT SVIA and SVIB peptides with IC$_{50}$ values above this threshold are not. More generally, the compounds of the invention are classified as antagonists of voltage-gated calcium channels by their ability to inhibit voltage-gated calcium channel currents with an ED$_{50}$ value of less than about 1 μM in the assay detailed in Example 1.

TABLE 1

Inhibition of calcium currents in N1E-115 neuroblastoma cells

| Compound | $IC_{50}$ |
| --- | --- |
| GVIA (SNX-124) | 10 nM |
| MVIIA (SNX-111) | 100 nM |
| SVIB (SNX-183) | >1 µM |
| SVIA (SNX-157) | >20 µM |

Calcium currents were also measured in human neuroblastoma IMR32 cells, using techniques described above and in Example 1. Voltage-gated calcium currents were elicited by holding the cell(s) at −70 mV and administering a step-voltage to −10 mV. Current tracings from IMR-32 cells bathed in control medium (lower curve) and in medium containing 150 nM SNX-111 (upper curve) are shown in FIG. 4A. The amplitude of the current is shown on the abscissa. The peak inward current is shown as the difference between the resting potential shown at the far left side of the figure and the lowest point of the curve, just adjacent to the resting value. In this experiment attenuation of voltage-gated calcium current is apparent in the presence of SNX-111 (upper curve), as shown by the decreased amplitude of the peak inward current.

FIGS. 4B and 4C show cumulative data from many consecutive currents, elicited at 15 second intervals as described above, in IMR-32 cells. In these plots, peak inward current recorded from each stimulus is recorded sequentially as a single data point. In the experiment illustrated in FIG. 4B, addition of SNX-111 to the bathing medium resulted in decreased peak inward currents; restoration of substantially normal calcium currents was achieved after washing of the compound from the cell chamber, shown on the right side of the figure. FIG. 4C shows the effects of 150 nM SNX-111 and SNX-183 added sequentially to a single cell preparation. Both compounds resulted in attenuation of peak inward current; though recovery following SNX-183 exposure was not observed. Addition of cadmium (Cd) to the medium resulted in blockade of all remaining voltage-gated calcium currents in this preparation.

Test peptides which are inhibitory for neuronal cell calcium currents can be further tested in non-neuronal cells, to confirm that the peptide activity in blocking calcium currents is specific to neuronal cells. A variety of muscle cell types which are refractory to calcium-current inhibition by OCTs, such as vertebrate embryo heart and skeletal muscle cells, are suitable. Cell current measurements are made substantially as outlined above and detailed in Example 1. OCT MVIIA, for example, has been reported to block voltage-gated calcium channels in a variety of neuronal cells, including dorsal root ganglion (DRG) neurons (McCleskey). This blockage or inhibition of calcium channel currents has been reported to be neuron-specific, since calcium current inhibition by the peptide was not observed in cardiac, smooth, and skeletal muscles.

B. Selective Inhibition of Norepinephrine Release

A second requisite property of neuroprotective compounds, in accordance with the invention, is the ability to specifically inhibit depolarization-evoked and calcium-dependent norepinephrine release in brain (CNS) neuronal cells, but not inhibit neurotransmitter release at a mammalian neuromuscular junction of a skeletal muscle. Inhibition of norepinephrine release in neuronal cells can be assayed in mammalian brain hippocampal slices by standard methods, such as detailed in Example 2. Briefly, hippocampal slices are distributed to individual wells of a microtitre plate, and incubated with radiolabeled norepinephrine under conditions favoring cell uptake. The cells are washed with a low-potassium medium, then bathed for 15 minutes in a high-potassium stimulation medium, in the presence of selected concentrations of the test compound. After removal of the stimulation buffer, radioactivity remaining in each slice is determined.

FIG. 5 shows effects of increasing concentrations of OCT MVIIA peptide on norepinephrine release from rat brain hippocampal slices which were first bathed in normal wash solution (open bars), then stimulation medium (solid bars). As seen, the compound produces a strong concentration-dependent inhibition of norepinephrine release in the presence, but not in the absence of stimulation medium. From the concentration-dependent inhibition data, the compound concentration effective to produce 50% inhibition of norepinephrine release ($IC_{50}$) is calculated.

The $IC_{50}$ values given in Table 2 for a variety of OCT peptides which have been examined by this method represent the average $IC_{50}$ values calculated from thin (200 µ) and thick (400 µ) hippocampal slices. The three lowest $IC_{50}$ values, between 0.8 and 2.4 nM, correspond to OCT peptides which show pronounced neuroprotective activity (Section III below). The OCT peptides SNX-195 and SNX-201 are OCT MVIIA with amino acid substitutions or modifications at key residue sites (FIG. 2), as will be discussed in Section IV below. The higher $IC_{50}$ values measured for these modified peptides is reflected in substantial reduction or loss of neuroprotective activity. Peptides SVIA (SNX-157) and SVIB (SNX-183) are representative of OCT compounds which show no neuroprotective activity, and this is reflected by high $IC_{50}$ values for norepinephrine release. The SNX-202 peptide is a modification of SVIB peptide in which the Ser-Arg-Leu-Met residues at positions 9–12 in OCT MVIIA (SNX-111) are substituted for the Arg-Lys-Thr-Ser residues at the same positions in OCT SVIB (SNX-183). This modification significantly reduced the $IC_{50}$ value for inhibition of norepinephrine release, but neuroprotective activity was not observed at a dose (2 µg ICV) at which SNX-111 generally provided neuroprotection.

TABLE 2

Inhibition of Norepinephrine Release by OCT Peptides

| OCT Peptides | $IC_{50}$ (nM) |
| --- | --- |
| GVIA (SNX-124) | 0.8 |
| MVIIA (SNX-111) | 1.5 |
| TVIA (SNX-185) | 2.4 |
| SNX-201 | 11 |
| SNX-195 | 11 |
| SNX-202 | 29 |
| SVIB (SNX-183) | 200 |
| SNX-191 | >100 |
| SVIA (SNX-157) | >4500 |

In summary, pronounced neuroprotective activity is associated with an ability to inhibit norepinephrine release with an $IC_{50}$ in the range 0.8–2.4 nM, and more generally with an $IC_{50}$ value which is within the range of $IC_{50}$ values measured for active OCT peptides MVIIA (SNX111), GVIA (SNX-124), and TVIA (SNX-185); i.e., less than the largest of the $IC_{50}$ values measured for these active OCT peptides. Compounds with $IC_{50}$ values slightly outside this range may have moderate to low neuroprotective activity, and compounds with high $IC_{50}$ values are not neuroprotective.

C. Specific, High Affinity Binding to OCT Receptors

Another property of neuroprotective compounds, in accordance with the invention, is high-affinity binding for an OCT MVIIA (SNX-111) binding site in neuronal cells. As will be seen below, the binding affinity can be characterized either by the binding constant of the compound for the MVIIA (SNX-111) binding site, or by the ratio of binding constants measured for binding to neuronal-cell MVIIA binding site and SVIB (SNX-183) binding site.

Binding to OCT MVIIA binding site in neuronal tissue can be demonstrated with a variety of cell types and synaptosomal cell fractions. One preferred neuronal membrane is a mammalian brain synaptosomal preparation, such as the rat brain synaptosome preparation described in Example 3. The binding constant of a compound for the MVIIA binding site is typically determined by competitive displacement of radiolabeled OCT MVIIA (SNX-111) from the synaptosomal preparation, as follows.

The binding constant $K_d$ of the MVIIA (SNX-111) peptide for the synaptosomal membranes is determined by a saturation binding method in which increasing quantities of radiolabeled peptide are added to the synaptosomal membranes, and the amount of labeled material bound at each concentration is determined. The plot of bound peptide as a function of concentration is then used to calculate a $B_{max}$, the concentration of binding sites on the synaptosomes, and $K_d$ following standard methods. In particular, the $K_d$ value is the calculated concentration of peptide needed to half saturate the synaptosomal specific binding sites. FIG. 6A shows the specific binding of radiolabeled OCT MVIIA (SNX-111) to rat brain synaptosomes, plotted as a function of OCT peptide concentration, and FIG. 6B, the same data in Scatchard plot form. From the slope of the Scatchard plot line, a $K_d$ binding value of 8.8 pM is obtained.

To determine the binding constant of a test compound for the MVIIA binding site, the test compound is added, at increasing concentrations to the synaptosome preparation having bound, radiolabeled OCT MVIIA. The synaptosomal material is then rapidly filtered, washed and assayed for bound radiolabel. The binding constant $(K_d)$ of the test compound is determined from computer-fit competitive binding curves, such as shown in FIG. 7 for MVIIA (SNX-111) peptide, to determine first the $IC_{50}$ value of the compound, i.e., the concentration which gives 50% displacement of labeled MVIIA peptide, then calculating K from the $K_d$ value of OCT MVIIA and the $IC_{50}$ value of the compound, as detailed in Example 4. A relative potency value can also be calculated from this information, as detailed in Example 4. Like the $K_i$ value, this value allows comparisons between assays performed at different times. Calculated $IC_{50}$ values for a number of OCT peptides which were examined are given in Table 3. The compounds are arranged in order of increasing $IC_{50}$ and $K_i$ values.

TABLE 3

| Competition of $^{125}$I-MVIIA (SNX-111) Binding by OTC Peptides | |
|---|---|
| | $IC_{50}$ (nM) |
| SNX-207 | .007 |
| SNX-194 | .008 |
| SNX-195 | .009 |
| MVIIA (SNX-111) | .013 |
| SNX-190 | .021 |
| SNX-200 | .039 |
| SNX-201 | .046 |
| SNX-202 | .046 |

TABLE 3-continued

| Competition of $^{125}$I-MVIIA (SNX-111) Binding by OTC Peptides | |
|---|---|
| | $IC_{50}$ (nM) |
| SNX-193 | .070 |
| MVIIB (SNX-159) | .101 |
| GVIA (SNX-124) | .134 |
| SNX-198 | .160 |
| SNX-191 | .160 |
| TVIA (SNX-185) | .228 |
| SNX-196 | .426 |
| RVIA (SNX-182) | .893 |
| SVIB (SNX-183) | 1.09 |
| GVIIA (SNX-178) | 3.70 |
| SNX-197 | 11.3 |
| SVIA (SNX-157) | 1460. |

Compounds with known neuroprotective activity, such as SNX-207, OCT MVIIA (SNX-111), GVIA (SNX-124), and TVIA (SNX-185), have $IC_{50}$ values between about 15 and 300 pM, and $K_i$ values between about 1 and 100 pM. Conversely, OCT peptides, such as OCT SVIA (SNX-157) and SVIB (SNX-183), which are not neuroprotective have substantially greater $IC_{50}$ and $K_i$ values.

A number of OCT peptide compounds which were tested gave $IC_{50}$ and $K_i$ values lower than or within the ranges of those of OCT peptides MVIIA (SNX-111), GVIA (SNX-124), and/or TVIA (SNX-185), and these compounds should thus be considered candidates as neuroprotective compounds. However, some of these compounds, such as SNX-201, SNX-195, and SNX-202 have $IC_{50}$ values for inhibition of norepinephrine release which are outside the range of neuroprotective compounds (Table 2), and thus these compounds do not meet all of the criteria for neuroprotective compounds.

The identity of the MVIIA binding protein in neuronal-cell membranes was examined by binding radiolabeled OCT MVIIA to synaptosomes, and crosslinking to peptide to neuronal membranes, as detailed in Example 5. The labeled membranes were solubilized with sodium dodecyl sulfate (SDS), fractionated by polyacrylamide gel electrophoresis (PAGE), and examined by autoradiography for labeled bands. In one case, the membranes were incubated with labeled peptide in the presence of excess unlabeled OCT MVIIA. A similar binding study was carried out with labeled OCT GVIA.

Autoradiographs of the gels are shown in FIG. 8, where lanes a and b show MVIIA (SNX-111) binding patterns to synaptosomal membranes in the absence (lane a) and presence (lane b) of unlabeled OCT MVIIA (SNX-111), and lanes c and d show GVIA binding patterns to synaptosomal membranes in the absence (lane c) and presence (lane d) of unlabeled OCT GVIA (SNX-124). The gel patterns show (lane a) most of the labeled SNX-111 peptide binds to a 200–210 kilodalton protein band, and that the binding is specific, as evidenced by displacement with unlabeled OCT MVIIA (SNX-111) (lane b). This binding also appears to be a major specific binding site of OCT GVIA (SNX-124), as judged from the radiolabeled patterns in lanes c and d.

It has also been discovered, in accordance with the invention, that compounds with highest neuroprotective activity show relatively low binding affinity for a second OCT binding site, defined by binding of OCT SVIB (SNX-183) binding to neuronal membranes, whereas high binding affinity for this site is observed with some inactive compounds. $IC_{50}$ and $K_i$ values for compound binding to this binding site can be calculated, as above, by determining the $K_d$ of OCT SVIB (SNX-183) binding to a synaptosome preparation, then using competitive displacement of labeled OCT SVIB by the test compound, to determine the $IC_{50}$ and $K_i$ values of the test compound. FIG. 9 shows computer-fit competitive binding curves for several OCT peptides whose binding to the SVIB (SNX-183) binding site was examined. From these curves, $IC_{50}$ and $K_i$ values were determined as above.

Table 4 shows the relative potencies for displacement of radiolabeled OCT MVIIA (SNX-111) and SVIB (SNX-183) for the compounds examined, calculated as described in Example 4. As seen, neuroprotective compounds OCT MVIIA (SNX-111), GVIA (SNX-124), SNX207 and TVIA (SNX-185) exhibited highest relative potencies at the MVIIA site. Although a general inverse correlation between neuroprotective activity and relative potency of binding at the SVIB (SNX-183) binding site is observed with some of the modified compounds, e.g., SNX-201, it is not seen with others, e.g., SNX-195. Table 4 also shows ratios of relative potencies of binding for each compound at the MVIIA and SVIB binding sites. These ratios accentuate the difference in binding properties between neuroprotective compounds, and those which show no neuroprotective activity within the range of concentrations tested.

TABLE 4

Relative Potencies of OCT Peptides at OCT Binding Sites

| | Relative Potency | | Ratio |
|---|---|---|---|
| | MVIIA Site | SVIB Site | MVIIA/ SVIB |
| MVIIA (SNX-111) | 1 | .02 | 45. |
| GVIA (SNX-124) | .072 | .014 | 5 |
| TVIA (SNX-185) | .04 | .00094 | 46 |
| SNX-207 | 1.5 | .0019 | 789. |
| SNX-195 | 59. | .012 | 4916 |
| SNX-218 | .054 | .019 | 2.8 |
| SNX-201 | .25 | .49 | 0.5 |
| SNX-202 | .24 | .33 | 0.7 |
| SNX-183 | .012 | 1.0 | 0.01 |
| SNX-157 | $7 \times 10^{-7}$ | $4.1 \times 10^{-5}$ | 0.02 |

From the foregoing, it is seen that neuroprotective compounds in accordance with the invention are characterized by a high binding affinity for the MVIIA binding site on neuronal membranes. The binding affinity for this site may be characterized in one of two ways. In the first approach, the binding affinity of the compound for the MVIIA site, as estimated by $IC_{50}$ at the site, is compared directly with those of SNX-111, SNX-207, SNX-124, or SNX-185. A neuroprotective compound is one whose binding affinity is at least as high as and preferably within the range of binding affinities measured for the OCT's MVIIA (SNX-111), GVIA (SNX-124), and TVIA (SNX-185), i.e., the binding constant is no greater than the highest binding constant among these four OCT peptides.

Alternatively, the binding affinity for the MVIIA site can be characterized by the ratio of binding constants or relative potencies for the MVIIA and SVIB sites, as just described. Here a neuroprotective compound is one whose binding ratio is within the range of such binding ratios measured for the OCT's SNX-207, MVIIA (SNX-111), GVIA (SNX-124), and TVIA (SNX-185), i.e., the binding ratio is no lower than the smallest ratio among these four OCT peptides.

III. Neuroprotective Compositions and Methods of Reducing Neuronal Damage Related to an Ischemic Condition The present invention provides a method and composition of the invention effective to reduce neuronal damage related to an ischemic condition in a human patient. The ischemic conditions may be due to an interruption in cerebral circulation, such as caused by cardiac failure, or other condition leading to global loss of blood supply to the brain, or to localized interruptions in blood flow, such as due to cerebral hemorrhage, or localized thrombotic or embolic events, or head trauma.

The ischemic condition which is to be treated using the method and composition is generally associated with stroke, defined as the sudden diminution or loss of neurological function caused by an obstruction or rupture of blood vessels in the brain, or by complete cessation of blood flow to brain, as in cardiac failure. In stroke, as well as in other types of cerebral ischemic conditions, the treatment method is aimed at preventing or reducing secondary brain damage resulting from the original ischemic event. The secondary damage typically includes cerebral cell destruction, or lesions, in the area surrounding the ischemic injury, in the case of focal ischemia, and also in areas of selective vulnerability, such as the hippocampus or basal ganglia, in the case of global ischemia. The secondary damage may often be manifested by functional impairment, such as loss of short-term or long-term memory. As will be seen below, the treatment method of the invention is effective in reducing or preventing both anatomical and functional secondary damage related to ischemia.

The composition of the invention includes a neuronal-cell calcium channel antagonist compound having activities for selectively blocking norepinephrine release in mammalian neuronal cells, and for binding to neuronal-membrane omega-conotoxin MVIIA binding site, which are within the ranges of such activities for OCT peptides SNX-207, MVIIA (SNX-111), GVIA (SNX-124), or TVIA (SNX-185). The binding activities may be expressed either as binding constants for the MVIIA site on neuronal membranes, or as a ratio of the binding constants for the MVIIA and SVIB binding sites, as discussed in Section II above. The compound is carried in a suitable pharmaceutical carrier, such as a sterile injectable solution.

One exemplary class of neuronal cell calcium channel antagonists is OCT peptides having the requisite inhibitory and binding activities. The peptide is formulated for parenteral administration in a suitable inert carrier, such as a sterile physiological saline solution. The concentration of peptide in the carrier solution is typically between about 0.1–20 mg/ml. The dose administered will be determined by route of administration. One suitable route is intracerebroventricular (ICV), at a dose level of about 0.1 to 20 μg peptide/kg body weight, depending on the binding and inhibitory values of the peptide. The peptide compound may alternatively be administered intravenously (IV) as demonstrated below. It may be desirable for IV administration to pretreat the subject with antihistamines specific for H1 and H2 histamine receptors, to reduce possible blood pressure lowering after peptide administration.

In the parent U.S. Pat. No. 5,051,403 and copending patent application U.S. Ser. No. 561,766, filed Nov. 22, 1989, and Aug. 2, 1990, respectively, the applicants have disclosed that omega-conotoxin peptides and related peptides which exhibit binding to and blockade of voltage-gated calcium channels are useful in reducing neuronal damage related to ischemic conditions. In the above-referenced applications, test compounds were administered at the time of or up to 1 hour following the experimentally induced occlusion which caused the ischemic event. As reported below, and according to an important feature of the invention, it has been found that there is little or no loss of protective effect of the neuroprotective compound when it is administered well after the ischemic event e.g., one hour following the period of transient occlusion. This delayed-administration protective event indicates that these compounds are effective in blocking the events leading from ischemic injury to secondary cerebral injury, since these events may occur over a period of many hours or even days after injury. Thus, the delayed administration may be effective to reduce secondary cerebral damage over a several hour period, or even a day or more, following the onset of ischemia.

The effectiveness of the composition in reducing neuronal damage related to ischemic injury has been examined in three animal systems which are widely employed as model systems for global ischemia and secondary stroke damage. The first system is the gerbil two vessel occlusion model of global ischemia produced by transient occlusion of carotid arteries of the neck. For clinical comparisons, the ischemia produced in this model has been likened to that produced by cardiac arrest, since all blood flow to the brain is stopped for a fixed period, typically 5–10 minutes.

Although some differences in particular sequelae have been noted among species, gerbils exhibit the same kind of selective regional damage from ischemia as is found in other mammals, including humans. In particular, the characteristic secondary damage observed in the hippocampal CA1 region is similar to that seen in other mammals, including humans (Kirino; Yamaguchi). Neurons in this area, and especially pyramidal neurons, exhibit a delayed neuronal death over a period of up to 4 days after ischemic injury.

The second animal model utilized in experiments carried out in support of the present invention is the rat four-vessel occlusion model. The experimental procedure for producing temporary occlusion produces an ischemia that mimics conditions in the human brain following cardiac arrest, including the following similarities: the ischemic event is temporary, typically 5–30 minutes; it occurs in an unanesthetized state; in most rats, the ischemic event is not accompanied by generalized seizures, and animals that have seizures can be excluded from the study. In addition, the occlusion procedure allows the animals to be easily monitored, maintained and analyzed (Pulsinelli).

The third animal model is the rat cerebral artery occlusion model of focal ischemia. In this model, the left middle cerebral artery is permanently occluded by electrocoagulation. Twenty-four hours after the occlusion, the animals are anesthetized and areas of damage are examined by magnetic resonance imaging.

A. Reduction in Anatomical Damage

Ischemia in the gerbil model system was induced in anesthetized animals by occluding the two carotid arteries for eight minutes, as detailed in Example 7. OCT peptide was administered ICV during the occlusion period, or one hour following occlusion. Four to five days after occlusion and peptide treatment, the animals were examined histologically for anatomical damage in the hippocampal CA1 region, as detailed in Example 7.

Figure 11A:
Figure 11B:
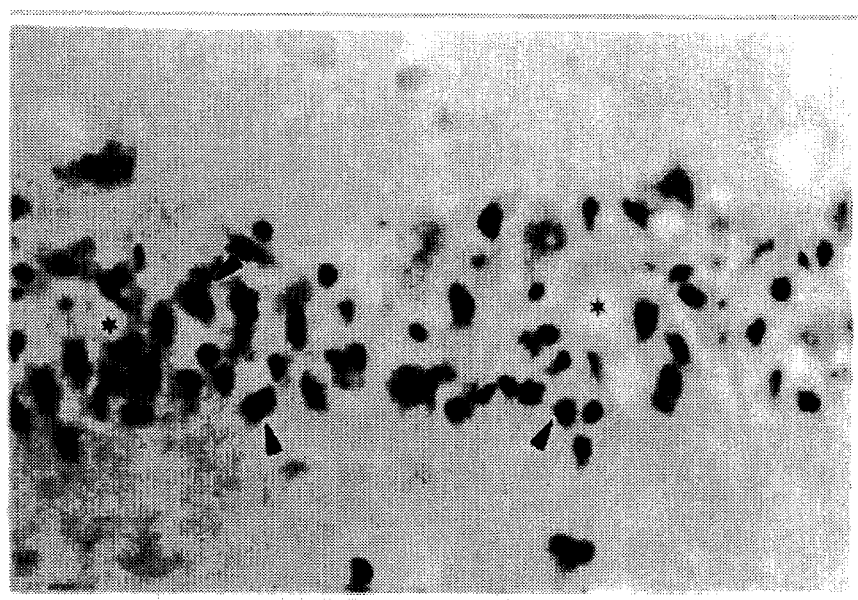
Figure 11C:
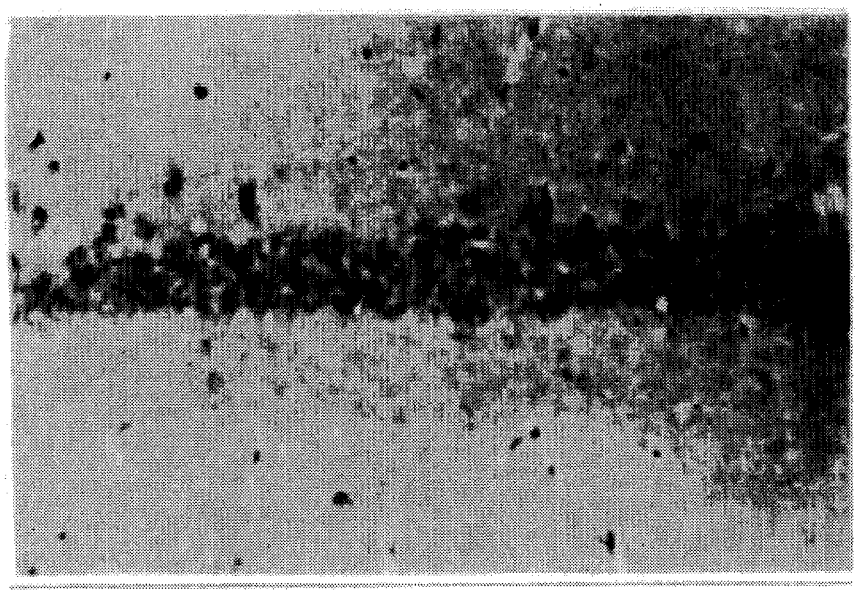
Figure 11D:
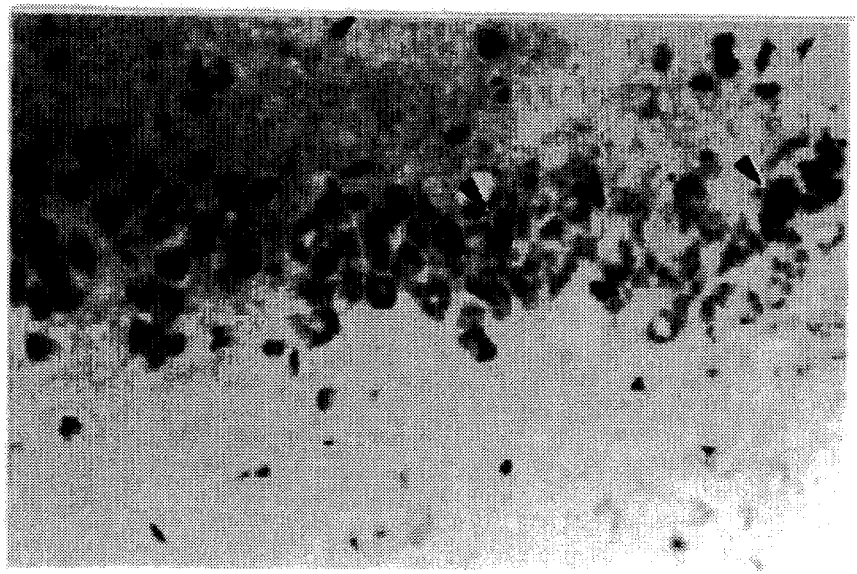

FIGS. 10A and 10B are low-power micrographs of gerbil hippocampus CA1 region in animals after ischemia, and infusion of MVIIA OCT (SNX-111) (10A) or drug vehicle (10B). The arrows in the figures indicate the approximate borders of the CA1 region. At higher power, cells in the drug-treated ischemic animals appear normal (FIG. 11A), whereas damage is apparent in the ischemic animals receiving vehicle alone (FIG. 11B). Another example of complete drug protection is seen in FIG. 11C, and an example of partial protection is seen in FIG. 11D, where there is a small number of damaged cells.

Anatomical sections, such as those seen in FIGS. 10 and 11, were scored according to the criteria set out in Example 7. The extent of anatomical damage in ischemic animals treated with OCT MVIIA (SNX-111) or OCT GVIA (SNX-124) or receiving vehicle alone (control), based on the above scoring system, is given in Table 5 below. The peptide was administered by ICV infusion during the eight minutes of ischemia, at a total dose indicated in the table below. As seen, the extent of damage in the higher-dose OCT MVIIA (SNX-111) treated animals was only 25% of that in untreated animals. The SNX-124 peptide also produced more than a 50% reduction in damage, and the lower dose showed near maximal effectiveness.

TABLE 5

Effect of OCT Peptides on Hippocampal Damage in Gerbils

| Treatment | N | Mean (SEM) Score | Percent Damage |
|---|---|---|---|
| Vehicle | 20 | 3.1 (.32) | 100% |
| 0.02 µg MVIIA (SNX-111) | 4 | 1.9 (.83) | 61% |
| 0.1 µg MVIIA (SNX-111) | 18 | ***0.8 (.09) | 25% |
| 0.02 µg GVIA (SNX-124) | 3 | *1.3 (.33) | 42% |
| 0.1 µg GVIA (SNX-124) | 11 | **1.2 (.39) | 39% |

*$p < .05$ compared to vehicle
**$p < .005$ compared to vehicle
***$p < .0005$ compared to vehicle A similar treatment method was applied in the gerbil global ischemia model, but the neuroprotective agent was administered 1 hour after the ischemic event. The observed reduction in anatomical damage is summarized in Table 6 below. A comparison of the data in Table 5 indicates little loss of protective effect at a comparable dose (0.1 µg) when the drug is administered 1 hour after the ischemic event (8 min of occlusion).

TABLE 6

Effect of OCT MVIIA (SNX-111) on Hippocampal Damage in Gerbils (1 hour post-ischemia)

| Treatment | N | Mean (SEM) Score | Percent Damage |
|---|---|---|---|
| Vehicle | 15 | 3.0 (.31) | 100% |
| 0.1 µg (SNX-111) | 16 | **0.9 (.13) | 30% |
| 0.3 µg (SNX-111) | 3 | ***0.7 (.17) | 23% |

**$p < .005$ compared to vehicle
***$p < .0005$ compared to vehicle

Ischemia in the rat model system was induced by first surgically closing the vertebral arteries, and after surgical recovery, transiently blocking the carotid arteries (thus completely blocking blood flow to the forebrain) for a period of 15 minutes. During occlusion, animals were given 0.3 µg SNX-111 ICV. Four days after occlusion, the animals were examined histologically to determine the extent of damage in the hippocampal CA1 region, as above. The mean scores are given in Table 7 for a comparison of saline and SNX-111 treatments. As seen, the extent of damage in the treated animals was only about ⅓ that in untreated animals.

Likewise, when SNX-207 was tested in the rat 4-VO model, as described above, significant neuroprotection was observed at doses of 3 and 10 μg, administered intraventricularly (Table 8).

TABLE 7

Effect of OCT MVIIA (SNX-111) on Hippocampal Damage in Rats by 4-VO (15 min. 4-VO)

| Treatment | N | Mean Score (SEM) |
| --- | --- | --- |
| Vehicle | 4 | 3.6 (0.38) |
| MVIIA OCT (SNX-111) (0.3 μg) | 5[a] | **1.2 (0.36) |

[a]Animals given MVIIA ICV were included in the study only if they exhibited characteristic shaking behavior.
**p < .005, unpaired Student's t test.

TABLE 8

Effect of SNX-207 on Hippocampal Damage in Rats by 4-VO

| Treatment | Dose | N | Mean Score (SEM) |
| --- | --- | --- | --- |
| Saline | — | 18 | 3.4 (0.5) |
| SNX-111 | 1 μg | 19 | ***1.4 (1.2) |
| SNX-207 | 3 | 19 | ***1.4 (1.3) |
| SNX-207 | 10 | 20 | ***1.5 (1.4) |

***p < .0001, compared to control unpaired student's t test

In separate studies, a series of additional OCT peptides were tested in the rat 4-VO model. The results of these studies are summarized in FIG. 12. Data were pooled from several experiments for this comparison. The data were subjected to Z-score transformation to facilitate comparison between samples having different mean control (saline treatment) damage values. In this analysis, the means of the control groups assume a value of zero, and deviations from the control are shown as positive (indicating an increase in damage compared to controls) and negative (indicating a decrease in damage compared to controls) values. OCT MVIIA (SNX-111) and OCT TVIA (SNX-185) each showed significant neuroprotection in the studies, as indicated from their significantly negative Z-scores. SNX-195, while not significantly different from control, did show a trend toward neuroprotection at the two doses tested, as indicated by its negative Z-scores at both doses. In contrast, OCT SVIB (SNX-183), SNX-202, SNX-201, and OCT SVIA (SNX-157) all showed no neuroprotective activity, as indicated by their positive Z-scores.

In a second treatment method, OCT peptide was administered intravenously, as detailed in Example 8B. The degree of neuroprotection in global ischemia produced by SNX-111 administered 1 hour post-occlusion is indicated in Table 9. "NSD" in the table indicates that the value is "not statistically different" from the saline control value. In this study a dose of 15 mg/kg SNX-111 was effective to confer significant protection against cerebral damage subsequent to cerebral ischemia.

TABLE 9

Effect of intravenous administration of OCT MVIIA (SNX-111) 1 hour post-occlusion on hippocampal damage in rats

| Treatment mg/kg | N | Mean Score | SEM | P |
| --- | --- | --- | --- | --- |
| Saline | 38 | 3.2 | .14 | — |
| 1 | 12 | 2.9 | .18 | NSD |
| 3 | 10 | 2.9 | .28 | NSD |

TABLE 9-continued

Effect of intravenous administration of OCT MVIIA (SNX-111) 1 hour post-occlusion on hippocampal damage in rats

| Treatment mg/kg | N | Mean Score | SEM | P |
| --- | --- | --- | --- | --- |
| 5 | 9 | 2.4 | .31 | NSD |
| 15 | 10 | 1.5 | .28 | P < .001 |

In the delayed administration paradigm of the rat 4 VO model, test compound was administered intravenously 6, 12, or 24 hours post-occlusion. Results of a study in which saline, 1, or 5 mg/kg of OCT MVIIA was given intravenously 6 hours post-occlusion are shown in Table 10. In contrast to administration 1 hour post-occlusion, when compound was given 6 hours post-occlusion, a significant reduction in neuronal damage was observed at the 5 mg/kg dose.

TABLE 10

Effect of intravenous administration of SNX-111 6 hours post-occlusion on hippocampal damage in rats

| Treatment mg/kg | N | Mean Score | SEM | P |
| --- | --- | --- | --- | --- |
| Saline | 11 | 2.8 | 0.35 | NSD |
| 0.2 | 11 | 2.4 | 0.34 | NSD |
| 1 | 10 | 1.8 | 0.36 | NSD |
| 5 | 8 | 0.9 | 0.34 | p = .002* |

*Significance determined by unpaired student's T test

Table 11 summarizes results from experiments in which rats were given 5 mg/kg OCT MVIIA 1, 6, 12, or 24 hours post-occlusion. For each time of administration, saline was administered to control animals for purposes of comparison. At this dosage, no significant protection was observed 1 hour post-occlusion; in contrast, the same dose produced significant neuroprotection when given at either 6, 12, or 24 hours post-occlusion.

TABLE 11

Comparison of effect of intravenous administration of MVIIA (SNX-111) (5 mg/kg) 1, 6 and 12 hours post-occlusion on hippocampal damage in rats

| Time | N[1] | Mean Score (SEM) Saline | Mean Score (SEM) MVIIA | P |
| --- | --- | --- | --- | --- |
| 1 hr | 38, 9 | 3.2 (.14) | 2.4 (.34) | NSD |
| 6 hrs | 11, 8 | 2.8 (.35) | 0.7 (.18) | p < .0001 |
| 12 hrs | 7, 7 | 2.7 (.55) | .71 (.09) | p < .0001 |
| 24 hrs | 7, 7 | 3.7 (.37) | 0.7 (.30) | p = .0001 |

[1]N values given for (saline, treated) groups.

In the third ischemia model system, the MCAO model of focal cerebral ischemia, OCT peptide was administered by ICV injection 10 minutes prior to occlusion of the left middle cerebral artery, as detailed in Example 9. Twenty-four hours later, the degree of anatomical damage in control and treated animals was examined by magnetic resonance imaging. Eight coronal images were recorded, and the infarct volume in each image was determined by counting pixels. Shown in Table 12 is the mean sum of pixels from eight coronal sections per rat. ICV treatment with 1.7 ug of SNX-111 resulted in a 24% reduction in the area of the mean infarct size produced by middle cerebral artery occlusion. This reduction was statistically significant, as assessed by the Mann-Whitney U test.

TABLE 12

Effect of OCT MVIIA (SNX-111) on Infarct Size

| Treatment (μg/rat) | N | Infarct Size Mean (SEM) | Percent Control | Statistical Significance |
|---|---|---|---|---|
| 0 | 6 | 5210 (290) | 100 | — |
| 0.6 | 6 | 4460 (330) | 87 | $2p > .05$ |
| 1.7 | 4 | 3880 (100) | 76 | $2p < .01$ |

B. Functional Activity Protection: Hyperactivity

One common consequence of cerebral ischemia in animals is hyperactivity, which can be seen as pacing (exploratory) behavior within a few hours of occlusion, and can be observed up to several days later. Hyperactivity in ischemic gerbils, was monitored as described in Example 10. Briefly, gerbils were tested individually for 60 min, with cumulative activity counts recorded every 15 min for statistical analysis. Baseline activity was measured before surgery to ensure comparability of the different treatment groups on this measure, and activity measurements were made at 1 and 3 days after occlusion.

The results of the tests are plotted in FIG. 13. The downward slope in each test curve is due to the decrease in activity over the four 15 minute intervals of the test (1–4 for baseline, 5–8 at day 1, and 9–12 at day three), as the animal becomes more familiar with the test environment. Occlusion alone (open triangles) produced a significant rise in activity level over baseline levels 1 day after occlusion, and an elevated activity level was observed over a three-day period, indicating permanent behavioral damage. Non-occluded control animals receiving ICV administration of vehicle (open circles) remained at baseline activity levels through the test period. OCT peptide itself, in the absence of ischemia (solid circles) reduced activity, and this effect persists slightly even at three days. Occluded animals which had been treated with OCT MVIIA (solid triangles) showed lower-than-baseline values at 1 day, apparently reflecting the reduced activity produced by the peptide alone. At three days, treated animals showed near-normal levels of activity, indicating that the OCT peptide treatment provided protection against ischemia-induced hyperactivity.

B. Functional Activity Protection: Spontaneous Alternation

Damage to the hippocampal region of the brain is known to produce deficits in spatial learning and memory, and therefore it could be expected that ischemic damage to hippocampal cells, as documented above, might also be accompanied by loss of functional activity related to short-term memory.

One test which has been widely applied as a measure of short-term memory in experimental animals is the Y maze, in which animals are placed at the base of the stem of a Y "maze" and allowed to enter either of the two Y arms When the animal enters an arm, a door is shut behind it. After 5 sec, the animal is returned to its home cage for an intertrial interval (ITI) of 2 to 12 min. At the end of that interval the animal is run in the maze again in the same way. Most normal animals will alternate, that is, will enter the arm that was not entered on the first trial. The test is scored by a "Y" for alternation and an "N" for repeat selection of the same Y arm.

In the test procedure, ischemia in gerbils was induced as above, with simultaneous ICV administration of vehicle (control) or 0.1 or 0.3 μg OCT MVIIA or GVIA peptide (results from all drug treatments were combined, as described in Example 10). Three days after occlusion, the animals were tested in the Y maze. Results of the spontaneous alternation tests are summarized in Table 13 for animals for which there was anatomical protection from doses of at least 0.1 μg of either compound.

TABLE 13

No. Gerbils Alternating (Y) or Repeating (N)

| Ischemia | Drug* | Experiment Number | | | | | | | | Combined | |
|---|---|---|---|---|---|---|---|---|---|---|---|
| | | 3 | | 4 | | 5 | | 6 | | Y | N |
| | | Y | N | Y | N | Y | N | Y | N | | |
| No | No | 9 | 3 | 2 | 2 | 3 | 3 | 6 | 2 | 20 | 10 |
| | Yes | — | — | 4 | 0 | 5 | 1 | 4 | 0 | 13 | 1 |
| Yes | No | 2 | 6 | 4 | 4 | 4 | 4 | 3 | 4 | 13 | 18 |
| | Yes | 4 | 3 | 5 | 2 | 7 | 1 | 7 | 4 | 23 | 10 |

*Drug doses are from 0.1 to 0.3 μg of MVIIA or GVIA.

As seen from the data in the table, the normal Y/N ratio for control animals (no occlusion, ICV administration of vehicle) was about 2:1. Ischemic injury produced a drop in this ratio to less than 1, indicating substantially random behavior in the Y test. The loss of short-term memory seen in ischemic animals was completely prevented by peptide treatment, with a Y/N ratio of about 2:1 being obtained. Peptide alone in the absence of ischemic injury appeared to enhance the Y/N ratio, and this enhancement may contribute to the improved performance of treated, ischemic animals.

In summary, ischemic animals in which OCT peptide treatment was shown to significantly reduce anatomical damage, also showed statistically improved functional activity, as evidenced by peptide protection against ischemia-induced hyperactivity and loss of short-term memory.

IV. Neuroprotective OCT Peptide Compounds

A. Selection of OCT Peptides

Based on a sequence homology analysis of the peptides whose full sequences are known (FIG. 1), the naturally occurring neuroprotective OCT peptides were grouped into distinct groups I and II, each with internal homologies distinct to that group, as can be appreciated from FIG. 14. Group I includes active OCT peptides MVIIA (SNX-111) and MVIIB (SNX-159) which possesses a binding constant to the MVIIA site within the range of compounds with neuroprotective activity. Group II includes neuroprotective peptides GVIA (SNX-124), TVIA (SNX-185) and SNX-207. A third group includes inactive peptides SVIA (SNX-157) and SVIB (SNX-183) and OCT peptides whose binding activities for the MVIIA site on neuronal membranes and/or activity in norepinephrine inhibition are outside the range of active compounds.

The three groups of OCT peptides are arranged in FIG. 14 with their six Cys residues aligned, which places these residues at positions 1, 8, 15, 16, 20, and 28. To make this alignment, gaps were introduced at the positions shown in the three groups. In the analysis below, these gaps retain the assigned number shown in FIG. 14, even though they represent amino acid deletions in the respective groups of active OCT peptides.

Sequence variation in the peptides, based on primary structure alone, was analyzed by adopting the following constraints:

1. The peptides in both active groups (I and II) include the Cys residues at position 1, 8, 15, 16, 20, and 28. Other Cys residues could be substituted at the positions indicated below only if they are selectively protected during oxidation of the peptide to form the three disulfide linkages.

2. The peptides in the active groups include three disulfide linkages connecting the Cys residues at positions 1 and 16, 8 and 20, and 15 and 28. As described above, the disulfide bridges are formed by air oxidation of the full sequence peptide in the presence of DTT. The ability of the peptide to form the three desired disulfide linkages would therefore require that the peptide, prior to disulfide bridging, be able to adopt a conformation which allows the three selected linkages, with or without the Cys protecting-group strategy discussed above. This constraint would thus exclude amino acid variations which prevent or otherwise hinder the formation of the three selected bridges.

Constraints 1 and 2 preserve the basic conformation of the OCT peptides imposed by the three disulfide bridges.

3. Within Group I, the amino acid variations which occur at the six non-conserved residues are allowed, including peptides in which the carboxy terminus is amidated or has a free acid form. That is, the first group compounds include the peptide structures having the form: SEQ ID NO: 22–$X_1$–SEQ ID NO: 23–$X_2$–SEQ ID NO: 25–$X_3X_4$–SEQ ID NO: 24–$X_5$–SEQ ID NO: 25–$X_6$–SEQ ID NO: 26–t, where $X_1$=K or S; $X_2$=S or H; $X_3$=L or T; $X_4$=M or S; $X_5$=N or a deletion; $X_6$=S or deletion, and t=a carboxy or amidated carboxyterminal group.

4. Within Group II, the amino acid variations which occur at the eight non-conserved residues are allowed, including peptides in which the carboxy terminus is amidated or has a free acid form. Thus, the second group compounds include the peptide structures having the form: SEQ ID NO: 23–$X_1$–SEQ ID NO: 27–$X_2X_3X_4$–SEQ ID NO: 28–$X_5X_6X_7$ –SEQ ID NO: 23–$X_8$–t, where $X_1$=K or L; $X_2$=X or R; $X_3$=T or L; $X_4$=S or M; $X_5$=T or S; $X_6$=K or R; $X_7$=R or K; and $X_8$=Y or R, and t=a carboxy or amidated carboxyterminal group.

5. Considering both active groups together, amino acid positions which are conserved in all active species are preserved. Thus, for example, the Cys residues, the 5-position glycine, the 13-position tyrosine, the 19-position serine, and the 26-position lysine are all preserved.

6. Considering both active groups together, there are amino acid positions which are likely to be variable within the range of active species. For example, the position 2 amino acid may be lysine or leucine, the position-3 amino acid may be glycine or serine, and the position 4 amino acid, hydroxyproline or arginine. In addition, if the two or more amino acids at a variant position are in a common substitution class, substitution within that class may be favorable. Standard substitution classes are the six classes based on common side chain properties and highest frequency of substitution in homologous proteins in nature, as determined, for example, by a standard Dayhoff frequency exchange matrix (Dayhoff). These classes are Class I: Cys; Class II: Ser, Thr, Pro, 4Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and cyclohexylalanine or a halogenated tyrosine in Group VI. Further, the classes may include both L and D stereoisomers, although L-amino acids are preferred for substitutions.

7. Considering the known inactive species, substitutions to amino acids which are present in inactive species, but not active ones, at any selected residue position, are not favored to preserve activity in the active compounds. Thus, for example, although a 3-position serine is present in both active and inactive compounds, 4-position serine or threonine is present in inactive species only, and either substitution is thus disfavored.

The above amino acid selection rules 6–7 are intended as a guide for allowed amino acid substitutions within neuroprotective OCT peptides. Once an amino acid substitution or modification is made, the peptide is further screened for the requisite calcium channel antagonist activity, and the requisite activities for inhibition of norepinephrine release and binding to the MVIIA (SNX-111) binding site of neuronal membranes, as described above.

Several of the amino acid substitutions or modifications to the OCT peptide illustrate the principles outlined above. For example, with reference to FIG. 2, the SNX-195 compound contains a Lys to Ala substitution at the position corresponding to position 26 in the MVIIA structure shown in FIG. 14. Since this substitution is at a conserved-sequence position, it is predicted that the neuroprotective activity would be lost or reduced. As seen above (FIG. 12), the SNX-195 peptide shows retention of MVIIA binding activity, but reduced norepinephrine release inhibitory activity, and weak neuroprotective activity compared with the unsubstituted MVIIA OCT.

As another example, the SNX-201 compound contains substitutions at positions 9—12 from Ser-Arg-Leu-Met to Arg-Lys-Thr-Ser, the sequence at positions 9–12 in the inactive SVIB OCT peptide. The position-9 substitution is not favored since Arg is present at this position in a non-neuroprotective compound, but not in one of the neuroprotective OCT peptides. The position-10 substitution is disfavored for the same reason. The position-11 substitution is favored, however, since the Leu to Thr substitution occurs within the neuroprotective peptides. The Met to Ser substitution at position 12 is favored for the same reason. Since the peptide modification contains two disfavored substitutions, it is predicted that the neuroprotective activity would be lost or reduced. As seen above, the SNX-201 peptide shows retention of MVIIA binding activity (Table 3), but reduced norepinephrine inhibitory activity (Table 2), and no neuroprotective activity at a concentration at which the unsubstituted MVIIA OCT/SNX-111 was found to be active (FIG. 12).

B. OCT Peptides

The invention further includes the active OCT peptides formed according to amino acid selection rules 3 and 4 above, excluding the natural C-terminal amidated OCT peptides MVIIA (SNX-111), MVIIB (SNX-159), GVIA (SNX-124), and TVIA (SNX-185). More specifically, the peptide compounds of the invention have the form: SEQ ID NO:22–$X_1$–SEQ ID NO: 23–$X_2$–SEQ ID NO: 25–$X_3X_4$–SEQ ID NO: 24–$X_5$–SEQ ID NO: 25–$X_6$–SEQ. I.D. No. 26–t, where $X_1$=K or S; $X_2$=S or H; $X_3$=L or T; $X_4$=M or S; $X_5$=N or a deletion; $X_6$=S or deletion, and t=a carboxy or amidated carboxyterminal group, excluding the peptides in which $X_1$=K, $X_2$=S, $X_3$=L, $X_4$=M, $X_5$=deletion, and $X_6$=S; and $X_1$=S, $X_2$=H, $X_3$=T, $X_4$=T, $X_5$=N, and $X_6$=deletion; and SEQ ID NO: 23–$X_1$–SEQ ID NO: 27–$X_2X_3X_4$–SEQ ID NO: 28–$X_5X_6X_7$–SEQ ID NO: 23–$X_8$–t, where $X_1$=K or L; $X_2$=X or R; $X_3$=T or L; $X_4$=S or M; $X_5$=T or S; $X_6$=K or R; $X_7$=R or K; and $X_8$=Y or R, and t=a carboxy or amidated carboxyterminal group, excluding the peptides in which $X_1$=K, $X_2$=X, $X_3$=T, $X_4$=S, $X_5$=T, $X_6$=K, $X_7$=R, and $X_8$=Y; and $X_1$=L, $X_2$=X, $X_3$=T, $X_4$=S, $X_5$=S, $X_6$=R, $X_7$=K, and $X_8$=R.

These peptides are intended for formulation with a suitable pharmaceutical carrier, in the composition of the invention.

V. Selecting Neuroprotective Compounds

The compound-test methods discussed in Section II can be used, also in accordance with the present invention, to identify calcium channel antagonist compound which have neuroprotective activity. In the screening method, a calcium channel antagonist compound is screened for its ability to inhibit norepinephrine release in mammalian CNS neuronal cells, and for its affinity for neuronal-cell omega-conotoxin MVIIA binding site. The calcium channel antagonist activity of the test compound may be known, or may be shown, e.g., by its ability to inhibit depolarization-evoked calcium channel currents in neuronal cells, as described in Example 1.

The test compound is selected for use in treating such neuronal damage if the compound:

(i) is effective in inhibiting norepinephrine release in mammalian CNS neuronal cells, in concentration ranges within which OCT peptides MVIIA, GVIA, SNX-207 and TVIA effectively inhibit such norepinephrine release, and (ii) has a binding affinity for the OCT MVIIA binding site which is within the range of binding affinities for the binding site of OCT peptides MVIIA, GVIA, SNX-207, and TVIA.

The compounds which can be screened include, in addition to OCT peptides, and analogs and fragments thereof, other peptide and peptide fragments and organic molecules. Preferred screening methods are described above, and detailed in Examples 2, 4, and 5.

V. Methods of Treatment

As demonstrated in Section IV, administration of compounds which are effective to inhibit neuronal calcium currents to animals subjected to a cerebral ischemic event results in reduction of neuronal damage. Surprisingly, as described above treatment with compounds of this class was shown to be effective, even when administration of the compound was delayed up to 24 hours following the onset of the ischemic event. This discovery has obvious implications and usefulness in the clinical setting, where time which elapses between an ischemic attack, such as a stroke, and diagnosis and treatment is typically at least several hours.

It is anticipated that compounds of the invention may be administered in any expedient formulation and route which results in delivery to the site of action, which is likely to be at or in close proximity to the ischemic region. Exemplary routes of administration are intracerebral and intravenous; however, it is appreciated that other routes of administration, including but not limited to intranasal, intrathecal, subcutaneous, or transcutaneous administration may be used in practicing the method of the invention.

The following examples illustrate, but in no way are intended to limit the present invention.

EXAMPLE 1

Calcium-Channel Antagonist Activity: Inhibition of Ionic Currents

Ionic currents through calcium channels were examined in cells that were voltage-clamped by a single patch-clamp electrode. These whole-cell patch-clamp studies were performed mainly on N1E115 mouse neuroblastoma cells, although a variety of cell types, including human neuroblastoma cell line IMR-32, have been examined.

A. Current Measurement Methods

Most measurements were obtained using a bath saline that allowed examination of the calcium currents in the absence of other ionic currents. These solutions contained 80 mM NMDG (as a sodium replacement), 30 mM TEACl (to block potassium currents), 10 mM $BaCl_2$ (as a charge-carrier through the calcium channels), and 10 mM HEPES at pH 7.3. Some solutions also contained 2 mM quinidine (to block potassium currents) and 3 µM tetrodotoxin (to block sodium currents). Normal bath saline was (mM): 140 NaCl, 10 glucose, 3 KCl, 2 $CaCl_2$, 1 $MgCl_2$, 10 mM HEPES pH 7.3. Intracellular solutions contained 150 mM CsCl, 0.5 mM $CaCl_2$, and all internal solutions were filtered before use.

Pipets were made from Corning 7052 glass (Garner Glass Company, Claremont, Calif. 91711), coated with Sylgard (Dow Corning, Midland, Mich. 48640) and fire-polished before use. Bubble numbers were typically 5 to 6, with pipet resistances typically 2–5 MOhms. Corning 8161, Kimble, and other glasses were also used without noticeable effect on the calcium currents observed.

Recordings were carried out at room temperature with an Axopatch 1-C amplifier (Axon Instruments, Foster City, Calif. 94404) and analyzed with pCLAMP software (Axon Instruments). Data were filtered at 1000 Hz for a typical sampling rate of 10.1 kHz; in all cases data were filtered at a frequency at most ⅕ of the sampling rate to avoid biasing. Data were collected on-line by the software. Analysis was performed on-screen with print-out via a Hewlett-Packard LaserJet Printer (Hewlett-Packard, Palo Alto, Calif. 94306).

The typical experiment was conducted as follows: after seal formation followed by series resistance compensation and capacitative transient cancellation, a voltage clamp protocol was performed wherein the cell potential was stepped from the holding potential (typically –100 mV) to test potentials that ranged from –60 mV to +20 mV in 10 mV increments. The cell was held at the holding potential for 5 seconds between pulses. Protocols starting from other holding potentials usually covered the same range of test potentials.

B. Current Inhibition Measurement

FIG. 3 shows calcium current traces from an N1E-115 mouse neuroblastoma cell. The figure is read from left to right in time, with downward deflections of the trace indicating positive current flowing into the cell. Currents were elicited by a voltage step from 100 mV to –10 mV. The cell was bathed in saline with sodium replaced by NMDG and 10 mM $Ba^{++}$ instead of 2 mM $Ca^{++}$. Potassium currents were blocked by TEA in the bath and $Cs^+$ in the pipet solution.

The three traces in FIG. 3, labeled B–D, show decreasing calcium currents, with increasing MVIIA OCT peptide concentrations of 10 nM (3B), 50 nM (3C), and 200 nM (3D).

The response of voltage-gated calcium current to increasing dosages of OCTs MVIIA and GVIA are shown in FIG. 4. The calculated $IC_{50}$ is approximately 10 nM for GVIA and 100 nM for MVIIA. These values indicate extremely high specificity of the peptides for their site of action.

Table 1 compares $IC_{50}$ values for GVIA, MVIIA, SVIB and SVIA OCTs. Whereas OCT GVIA and OCT MVIIA show 50% inhibition of the measured calcium current at nanomolar concentration range, $IC_{50}$ values for OCT SVIB and OCT SVIA were not measurable within the range of concentrations tested, and are therefore listed as having $IC_{50}$ values above the micromolar concentrations indicated. OCT SVIB and OCT SVIA are considered to be inactive in this assay.

EXAMPLE 2

Inhibition of Neurotransmitter Release

A. [$^3$H]Norepinephrine release from rat hippocampal slices.

Male Sprague-Dawley rats were lightly anesthetized with ether, decapitated, and the brains removed. The hippocampi were then dissected free of cerebral cortex and rinsed with room temperature oxygenated uptake buffer (0.1% bovine serum albumin (BSA), and in mM: NaCl, 123; KCl, 4.8; $CaCl_2$, 1.2; $MgSO_4$, 1.2; $KH_2PO_4$, 1.2; glucose, 11; $NaHCO_3$, 25). Slices (200 or 400 uM thick) were made using a McIlwain Tissue Chopper and were immediately transferred to room temperature uptake buffer. Slices were then distributed to individual wells of a 96-well plate (Dynatech) containing 0.1 ml uptake buffer per well. [3H] Norepinephrine (3 uCi/ml) diluted in uptake buffer containing 1 mM ascorbate and test compound was then added to each well. Incubation was at 37 degrees for 30 minutes in a humidified, 5% $CO_2$ incubator. Bathing buffer was then removed and slices washed two times for 11 minutes each with basal buffer containing appropriate test compound (basal buffer: 0.1% BSA and, in mM: NaCl; 123, KCl, 5.0; $CaCl_2$, 0.4; $MgSO_4$, 1.2; $KH_2PO_4$, 1.2; glucose, 11; $NaHCO_3$, 25). Each slice was then incubated for 15 minutes in 0.1 ml of basal buffer. This buffer was then removed for measurement and replaced by 0.1 ml stimulation buffer (0.1% BSA in mM: NaCl, 97; KCl, 30; CaCl2, 0.4; $MgSO_4$, 1.2; $KH_2PO_4$, 1.2; glucose, 11; $NaHCO_3$, 25) for 15 minutes. Stimulation buffer was then removed for measurement of radioactivity. Radioactivity remaining in each slice was determined. Data were normalized to total cpm of radioactivity per slice: total radioactivity=S+B+slice, where S is the amount of radioactivity present in the stimulation buffer, and B is the amount of radioactivity present in the basal buffer. Stimulated release, as a percentage of total radioactivity= 100 (S/(S+B+slice)), and basal release, as a percentage of total radioactivity=100 (B/(S+B+slice)). Concentration-effect graphs are plotted as in FIG. 5. Computer aided curve fitting was used to determine $IC_{50}$ values from such data.

EXAMPLE 3

Synaptosomal Membrane preparations

A. Mammalian-Brain Synaptosomes and Synaptosomal Membranes.

Synaptosomes were prepared from rat whole brain or hippocampal region of brain. Rats were sacrificed, and forebrains were removed and transferred to 10 ml ice-cold 0.32 M sucrose containing the following protease inhibitors (PI): 1 mM EGTA; 1 mM EDTA; 1 uM pepstatin; 2 uM leupeptin. Brains were homogenized using a motor-driven Teflon-glass homogenizer (approx. 8 passes at 400 rpm). Homogenates from 4 brains were pooled and centrifuged at 900 xg for 10 minutes at 4 degrees. Supernatants were then centrifuged at 8,500 xg for 15 minutes. Resulting pellets were resuspended in 10 ml each ice-cold 0.32M sucrose plus PI with vortex mixing. The suspension was then centrifuged at 8,500 xg for 15 minutes. Pellets were resuspended in 20 ml ice-cold 0.32 M sucrose plus PI. The suspension (5 ml/tube) was layered over a 4-step sucrose density gradient (7 ml each: 1.2M sucrose, 1.0M sucrose, 0.8M sucrose, 0.6M sucrose; all sucrose solutions containing PI). Gradient tubes were centrifuged in a swinging bucket rotor at 160,000 xg for 60 minutes at 4 degrees. The 1.0M sucrose layer plus the interface between the 1.0 and 1.2M sucrose layers were collected and diluted with ice cold deionized water plus PI to yield a final sucrose concentration of 0.32M. The resulting suspension was centrifuged at 20,000 xg for 15 minutes. Pellets were then resuspended in 5 ml ice-cold phosphate buffered saline plus PI. The resulting rat brain synaptosomes were then aliquoted and stored in a liquid nitrogen containment system.

Prior to use in binding assays, synaptosomes were thawed and diluted with 3 volumes of ice cold deionized water plus PI. This suspension was homogenized using a PT 10–35 Polytron (setting 6) for two 10-second bursts. The homogenate was centrifuged at 40,000 xg for 20 minutes at 4 degrees. The resulting pellets were resuspended in about 5 ml of ice cold phosphate buffered saline plus PI. The resulting brain synaptosomal membrane preparation was aliquoted and stored at -80° C. until use. Protein concentration of the membrane preparation was determined using Bradford reagent (BioRad), with bovine serum albumin as standard.

EXAMPLE 4

OCT Peptide Binding to MVIIA (SNX-111) Binding Site in Synaptosomal Membranes A. Saturation Binding Assay MVIIA OCT was radiolabeled with $^{125}$I-iodine by reaction with Iodogen™, essentially according to the method of Ahmad and Miljanich. Following the Iodogen reaction, the peptide solution was chromatographed by HPLC through a C-8 reversed phase column and eluted with a gradient from 0.1% trifluoroacetic acid in water to 0.1% trifluoroacetic acid in water/acetonitrile (40:60 vol/vol). The major peak of radioactivity following the underivatized MVIIA OCT was collected.

The binding constant ($K_d$) for [$^{125}$I]-MVIIA OCT to rat brain synaptosomal membranes was determined by a saturation binding method in which increasing quantities of [$^{125}$I]MVIIA OCT were added to aliquots of a synaptosomal membrane preparation (10 ug membrane protein, suspended in binding buffer consisting of 20 mM HEPES, pH 7.0, 75 mM NaCl, 0.1 mM EGTA, 0.1 mM EDTA, 2 μM leupeptin, 0.035 μg/ml aprotinin, and 0.1% bovine serum albumin (BSA), in a total volume of 0.5 ml). Binding at each concentration of labeled compound was determined in the absence and presence of 1 nM unlabeled MVIIA OCT to determine specific binding (as described in part B, below). The amount of labeled peptide specifically bound at each concentration was used to determine $B_{max}$, the concentration of specific binding sites on the synaptosomes, and $K_d$, following standard binding analysis methods (Bennett).

FIG. 6A shows a saturation binding curve of [$^{125}$I]MVIIA to rat synaptosomal membranes. FIG. 6B shows a Scatchard transformation of the data, from which a calculated $K_d$ of about 10 pM is determined.

B. Competitive Displacement Binding Assay

Rat brain synaptosomal membranes prepared as described in Example 3 were suspended in a binding buffer consisting of 20 mM HEPES, pH 7.0, 75 mM NaCl, 0.1 mM EGTA, 0.1 mM EDTA, 2 µM leupeptin, 0.035 µg/ml aprotinin, and 0.1% bovine serum albumin (BSA). [$^{125}$I]-MVIIA (SNX-111) OCT (25–30,000 cpm, approximately 1500–2000 Ci/mmol) and test compound were aliquoted into polypropylene tubes, in the absence or presence of 1 nM MVIIA (SNX-111) OCT to determine nonspecific binding. The membrane suspension was diluted and aliquoted last into the test tubes, such that each assay tube contained 10 µg membrane protein and the total volume was 0.5 ml. After incubation for 1 hour at room temperature, tubes were placed in an ice bath, then filtered through GF/C filters (Whatman), which were pre-soaked in 0.6% polyethyleneimine and prewashed with wash buffer (20 mM HEPES, pH 7.0, 125 mM NaCl, 0.1% BSA) using a Millipore filtration system. Just prior to filtration, each assay tube received 3 ml ice-cold wash buffer. The filtered membranes were washed with two 3 ml volumes of ice-cold wash buffer, dried, and filter-bound radioactivity was measured in a Beckman gamma counter (75% counting efficiency). Representative displacement binding curves for rat brain synaptosomal membranes are illustrated in FIG. 7. $IC_{50}$ values were computed from line fit curves generated by a 4-parameter logistic function. These values represent the concentration of test compound required to inhibit by 50% the total specific binding of [$^{125}$I]-MVIIA (SNX-111) OCT to rat brain synaptosomal membranes, where specific binding is defined as the difference between binding of [$^{125}$I]-MVIIA (SNX-111) OCT in the absence and presence of excess (1 nM) unlabelled MVIIA OCT. Non-specific binding is that binding of radiolabeled compound which is measured in the presence of excess unlabeled MVIIA OCT. Such values serve as approximations of the relative affinities of a series of compounds for a specific binding site.

The binding constant ($K_i$) for each test substance was calculated using non-linear, least-squares regression analysis (Bennett & Yamamura) of competitive binding data from 2 assays performed in duplicate on separate occasions. The relationship between $K_i$ and $IC_{50}$ (concentration at which 50% of labeled compound is displaced by test compound is expressed by the Cheng-Prusoff equation:

$$K_i = IC_{50}/(1+[L]/K_d)$$

where $IC_{50}$ is the concentration of test substance required to reduce specific binding of labeled ligand by 50%; [L] is the concentration of [$^{125}$I]-MVIIA (SNX-111) OCT used in the experiment; and $K_d$ is the binding constant determined for binding of [$^{125}$I]-MVIIA (SNX-111) OCT to rat brain synaptosomal membranes in saturation binding experiments. Table 3 summarizes computed $IC_{50}$ for various OCT peptides for the MVIIA binding site of rat brain synaptosomal membranes.

Relative potency for displacement of binding is calculated as a ratio of the $IC_{50}$ of the test compound and the $IC_{50}$ of the reference compound. The reference compound is generally the unlabeled equivalent of the labeled ligand. Calculation of relative potency is as follows:

$$[\log \text{(relative potency)}] = \log (IC_{50(ref)}) - \log(IC_{50(test)})$$

Relative potency values for binding at OCT MVIIA (SNX-111) and OCT SVIB (SNX-183) sites are listed in Table 4.

EXAMPLE 5

Identification of OCT MVIIA (SNX-111) Binding Protein

Synaptosomal membranes from rat brain hippocampal region (RHM) were prepared as described in Example 3. An aliquot of synaptosomal preparation containing 40 µg protein was diluted in cross-link binding buffer (20 mM HEPES, pH 7.1, 75 mM NaCl, 0.1 mM EDTA, 0.1 mM EGTA, 0.002 mM leupeptin, 0.5 TIU/ml aprotinin). This suspension was pelleted (13,000×g, 15 min.). The pellet was then resuspended in crosslink binding buffer, pelleted again, and the resulting pellet was suspended in crosslink binding buffer to give washed synaptosomal preparations having final protein concentrations of approximately 1 mg/ml.

Binding was carried out in a total volume of 0.5 ml, containing 0.4 ml of appropriate crosslink binding buffer, 0.05 ml of washed synaptosomal preparation (concentration of binding sites: (approximately 10 pM), and 0.05 ml of MVIIA (SNX-111) OCT (final concentration: 0.1 nM). In separate aliquots, 0.005 ml unlabeled MVIIA OCT was added to assess nonspecific binding (final concentration: 0.05 µM). Incubation was at 20–24° for 25 min., rotating samples end over end.

At the end of the incubation period, crosslinking of bound [$^{125}$I]-MVIIA OCT to its receptor was carried out by adding 0.01 ml of 25 mM 1-ethyl-3-(3-dimethylaminopropyl) carbodiimide HCl (EDC) to the suspension (EDC dissolved in 25 mM PIPES, pH 6.1, immediately prior to use). The mixture was incubated for ten minutes on ice, with intermittent mixing. The reaction was quenched by addition of 20 mM ammonium acetate. The mixture was then pelleted by centrifugation at 13,000×g for 15 min., and subsequently washed 1–2 times by resuspension in 25 mM HEPES buffer pH 7.5 and pelleting. The final pellet was dissolved in 20 µl fresh sample buffer (200 mM Tris-HCl, 10 mM dithiothreitol, 4M urea, 8% SDS, 10% glycerol, 0.1% bromphenol blue), then subjected to SDS PAGE (4–15% acrylamide gradient gel) without prior heating of the sample. Similar experiments were carried out, using [$^{125}$I]-GVIA OCT as crosslink ligand.

FIG. 8 shows an autoradiogram demonstrating the crosslinked binding of [$^{125}$I]-MVIIA OCT and [$^{125}$I]-GVIA OCT to rat brain synaptosomal membrane preparations. Although a number of protein bands were labeled by the procedure, binding at a protein band migrating as a 200–230 kilodaltons protein was specifically displaced by inclusion of excess unlabelled ligand as described above.

These results suggest that high affinity specific binding to rat synaptosomal membranes is at least in part attributable to binding at a protein band which migrates in the 200–230 Kd region on a gel. Labeling of other bands may be due to either lower affinity or non-specific binding, since labeling to these bands was not displaced by unlabeled ligand.

EXAMPLE 6

OCT Peptide Binding to SVID (SNX-183) Binding Site in Synaptosomal Membranes

Rat brain synaptosomal membranes were prepared as described in Example 3. OCT SVIB was radiolabeled by iodination with $^{125}$I-iodine by the Iodogen reaction, described in Example 4. Displacement binding of radiolabeled SVIB on rat brain synaptosomal membranes was carried out as in Example 4B. SVIB displacement curves for several of the OCT peptides assayed is shown in FIG. 9. $IC_{50}$ values and relative potency values were calculated as described in Example 4. Table 4 shows the relative potency values for OCT peptides examined, and the ratio of relative potencies of the compounds for the OCT MVIIA site and to the SVIB binding site.

EXAMPLE 7

Reduction in Anatomical Damage: Global Ischemia Model 1

Global ischemic damage was examined in the gerbil model, according to standard procedures (Kirino). Male mongolian gerbils (*Meriones unguiculatus*, Tumblebrook Farm, West Brookfield, Mass.) weighing 50–80 g were anesthetized in a small chamber with 4% halothane carried by 70% nitrous oxide (0.44 L/min) and 30% oxygen (0.19 L/min). They were then maintained throughout surgery with 2% halothane by placing their noses through a hole in a rubber dam on a gas delivery tube. Using aseptic techniques, both common carotid arteries were exposed, dissected free of surrounding tissue, and occluded with microvascular clamps approximately 3 to 4 mm above the clavicle. The occlusions were maintained for 8 minutes, timed while both arteries were occluded. There was generally a period of approximately 1 minute between clamping of each of the two arteries, and approximately 4 seconds between unclamping them. After the clamps were removed, the skin was sutured shut and anesthesia discontinued.

During or after the occlusion, an intracerebroventricular (ICV) injection aimed at the lateral ventricle was made. To accomplish this, a 10 microliter Hamilton syringe with a 27 gauge needle was filled with injectate by backloading to assure the absence of air in the system. A stiff plastic sleeve was slipped onto the needle so that 3.5 mm of the needle protruded past the sleeve. The skull around the bregma was exposed, a distance of 1.1 mm left of the midline was measured with a compass, and a distance of 0.4 mm posterior to bregma was approximated by eye. The needle tip was held perpendicular to the skull and inserted through it at that point by applying gentle pressure while twisting. It was advanced until the sleeve abutted the skull, and 5 microliters of injectate was infused over a period of approximately 3 sec. The skin was then sutured shut. Occluded animals received either drug or its vehicle. Injected, unoccluded controls were anesthetized, and received the ICV injection only.

Four to five days after the initial occlusion, animals were anesthetized with $CO_2$. The chest cavity was opened and the animal was perfused through the heart with approximately 3 milliliters of phosphate-buffered saline (PBS; 0.10M sodium phosphate; 0.15M sodium chloride) containing heparin (10 Units/ml), followed by approximately 10 ml of Zamboni's fix (15% (vol/vol) picric acid, 4% (wt/vol) paraformaldehyde in 0.1 M phosphate buffer pH 7.4) or 10% phosphate buffered formalin. Brains were removed and left immersed in the same fixative for several hours.

Brains were blocked just posterior to the optic chiasm and posterior to the mammillary bodies. They were then placed in 10% (wt/vol) sucrose in PBS overnight at 4 degrees. The block containing the hippocampus was frozen with liquid Freon onto a cryostat chuck using Tissue-Tek™ O.C.T. embedding medium for frozen tissue specimens (Miles Inc., Elkhart, Iowa). Sections 10 microns in thickness were cut. Series of 5 sections were collected, with each series approximately 100 microns apart, until the relevant part of the hippocampus was obtained (40–50 sections per brain). At least 8 sections per brain were stained with hematoxylin and eosin, substantially according to reported procedures.

Coverslips were then placed over the sections, using Permount™ as an adhesive. FIGS. 10A and 10B are low-power micrographs of gerbil hippocampus (CA1 region) in animals after ischemia, after infusion of MVIIA OCT (10A) or after drug vehicle (10B). The arrows in the figures indicate the approximate borders of the CA1 region of the hippocampus. At higher power, cells in the drug-treated ischemic animals appear normal (FIG. 11A), whereas damage is apparent in the ischemic animals receiving vehicle alone (FIG. 11B). Another example of complete drug protection is seen in FIG. 11C, and an example of partial protection is seen in FIG. 11D, where there are a small number of damaged cells.

Sections, such as those seen in FIGS. 10 and 11, were viewed and scored by an investigator having no knowledge of the treatment of any particular sample. Ischemic damage was scored in the CA1 region of the hippocampus. Damage was generally seen as pink (eosinophilic) cytoplasm and shrunken, dark blue nuclei. Scoring was as described below:

| Score | Observation |
|---|---|
| 0 | No damaged cells were apparent. |
| 1 | Less than 25% damaged cells in a CA1 field, or damage was restricted only to the extreme edges of the CA1 region. |
| 2 | Approximately 50% damaged cells in a CA1 field, or damage to less than half the length of CA1, but more than to only the extreme edges. |
| 3 | Damaged cells outnumber normal cells to a maximum of 75%, with damage extending throughout most of CA1. |
| 4 | Complete damage to CA1, with fewer than 25% normal cells surviving. |

The extent of anatomical damage in ischemic animals treated with MVIIA or GVIA OCT or receiving vehicle alone (control), based on the above scoring system, is given in Table 5. The peptide was administered by ICV infusion during the eight minutes of occlusion, at a total dose indicated in Table 5. As seen, the extent of damage in the higher-dose MVIIA OCT treated animal was only 25% of that in untreated animals. The GVIA peptide also produced more than a 50% reduction in damage, and the lower dose was near maximal effectiveness.

In a second treatment method, the OCT peptide was administered by ICV infusion 1 hour after the 8-min occlusion, at the same drug dosage level as indicated above. The anatomical damage in the presence and absence of drug, scored as above, is given in Table 6.

EXAMPLE 8

Reduction in Anatomical Damage: Global Ischemia Model 2

Global ischemic damage was examined in the rat brain model, employing the four-vessel occlusion method of Pulsinelli and Briefly (Pulsinelli) for introducing temporary global ischemia in rats. Although the two carotid arteries supply blood to the forebrain, their occlusion alone has only moderate effects on forebrain blood flow because the posterior communicating arteries allow blood to be shunted from the brainstem blood supply, which is fed by the two vertebral arteries. Therefore, in order to effect severe forebrain ischemia, all four vessels must be occluded. The procedure used allows ischemia to be produced in conscious animals, by closing surgically implanted clamps, and therefore avoid possible interactions with drug treatment. The procedure was modified to allow carotid occlusion without the need for reopening a skin wound in conscious animals.

Surgery was performed to permanently occlude both vertebral arteries and to implant an arterial clasp to allow temporary occlusion of the carotid arteries at a later time. Under sodium pentobarbital anesthesia (60 mg/kg) male Fisher 344 rats were placed in a stereotaxic holder and the first cervical vertebra was exposed with the aid of a dissecting microscope. The vertebral arteries were occluded through the alar foramina with a thermocautery device and the skin closed with wound clips. The animal was placed on its back and the carotid arteries were carefully dissected free of the surrounding nerves and vessels under the microscope. The loose end of the Silastic loop of the clasp was passed behind the artery and put through the open side of the clasp and secured as for the other end. This was then repeated for the other carotid. The clasps were tied into the skin with 3-0 suture as the skin was closed so as to externalize the ends of the loop.

Ischemia was produced 2 days after surgery. To occlude the carotid arteries, the animal was held by lightly pinching the skin at the back of the neck and the ends of each loop were pulled out and secured with a bulldog clamp. At the end of the 15 min. occlusion, the clamps were removed to allow reperfusion. An effective occlusion causes the animal to lose its righting response within about 1 min. of occlusion. If the animal did not lose the righting response or if it regained it during occlusion, the loops were pulled tighter to assure complete carotid occlusion. Animals that did not lose their righting response were eliminated from the study, because this suggested that there was still significant cerebral blood flow.

Neuropathological analysis (see below) of such animals has confirmed this observation, because the damage is found to be less than in animals that do lose their righting response. Some animals righted themselves once or twice during the occlusion but immediately lost the righting response again, and were not eliminated from the study. Any animal that righted itself and remained up was eliminated.

A. Intracerebroventricular Administration of OCT Peptide

Rats receiving intracerebroventricular (ICV) compound were anesthetized using halothane immediately following reperfusion, and compound contained in 5 µL saline or saline alone was injected into the lateral ventricle as for gerbils. The coordinates of the injection were 1.2 mm left of midline and 0.5 mm posterior to bregma, at a depth of 3–4 mm. Rectal temperature was monitored from just before occlusion, and for 4–6 hours post occlusion. Rats were maintained normothermic (rectal temperature at about 37 degrees) for 4–6 hours following occlusion, by means of a heating apparatus. The degree of neuroprotection was assessed as in Example 7 and is shown in Tables 7 and 8.

B. Intravenous Administration of OCT Peptide

For intravenous (IV) administration of compound in conjunction with the rat 4-VO model of cerebral ischemia, rats were subjected to surgery and subsequent occlusion as described above. For administration of compound, rats were placed into Rodent Restraint Cones (Harvard Bioscience). Reversible tourniquets were applied to tail veins, and OCT compound was injected in a total volume of 0.25 ml, at the times and doses indicated in Tables 8–11. As in the case of ICV administration, rats were maintained normothermic (rectal temperature at about 37 degrees) for 4–6 hours following occlusion, by means of heating apparatus. The degree of neuroprotection was assessed as in Example 7 and is shown in Table 9.

EXAMPLE 9

Reduction in Anatomical Damage: Focal Ischemia Model

The rat middle cerebral artery occlusion model of cerebral ischemia was performed on SHR strain rats. Rats were anesthetized using Evipan (150 mg/kg i.p.). OCT MVIIA (SNX-111) was injected in a volume of 5 ul intracerebroventricularly into the left lateral ventricle, as described in Example 8. Within 10 minutes, the left middle cerebral artery was permanently occluded by electrocoagulation. Twenty four hours after the occlusion was performed, rats were again anesthetized with Evipan for magnetic resonance imaging. Eight coronal images were recorded. The infarct area in each image was determined by counting pixels. Shown in Table 12 is the mean sum of pixels from eight coronal sections per rat. Treatment with 1.7 ug of MVIIA OCT (i.c.v) resulted in a 24% reduction in the volume of the mean infarct size produced by middle cerebral artery occlusion. This reduction was statistically significant, as assessed by the Mann-Whitney U test.

EXAMPLE 10

Protection Against Loss of Functional Activity

A. Hyperactivity

One common sequela of cerebral ischemia is hyperactivity, which can be seen as pacing behavior within a few hours of occlusion and can be measured up to several days later. Hyperactivity was quantitated with Automex activity monitors (Columbia Instruments, Columbus, Ohio), which record perturbations of a radiofrequency field. Gerbils were tested individually in 17×27-cm plastic cages for 60 min, with cumulative activity counts recorded every 15 min for statistical analysis. Baseline activity was measured before surgery to ensure comparability of the different treatment groups on this measure.

The results of the tests are plotted in FIG. 13. The downward slope in each test curve is due to the decrease in activity over the four 15 minutes intervals of the test (1–4 for baseline, 5–8 at day 1, and 9–12 at day three), as the animal becomes more familiar with the test environment. Occlusion alone (open triangles) produced a significant rise in activity level over baseline levels 1 day after occlusion, and an elevated activity level was observed over a three-day period, indicating permanent behavioral damage. Non-occluded control animals receiving ICV administration of vehicle (open circles) remained at baseline activity levels through the test period. OCT peptide itself, in the absence of ischemia (solid circles) reduces activity, and this effect persists slightly even at three days. Occluded animals which had been treated with OCT MVIIA (solid triangles) showed lower-than baseline values at 1 day, apparently reflecting the reduced activity produced by the peptide alone. At three days, treated animals showed near-normal levels of activity, indicating that the OCT peptide treatment provided protection against ischemia-induced hyperactivity.

B. Spontaneous Alternation

Because the predominant neuropathological consequence of the type of ischemia used here is hippocampal damage (Example 7) which is known to produce deficits in spatial learning and memory, a test of recent (working) memory in maze performance was employed. This test uses a Y maze.

Gerbils were tested in a Y maze, in which the animal is placed in the base of the stem of the maze, and when the animal enters an arm, a door is shut behind it. After 5 sec, the gerbil is returned to its home cage for an intertrial interval (ITI) of 2 to 12 min. At the end of that interval the gerbil is run in the maze again in the same way. Most normal animals will alternate, that is, will enter the arm that was not entered on the first trial. Occasionally an animal did not enter an arm within about 1 min. because it had a seizure, so it was eliminated from that test.

Because individual experiments include too few animals per group to allow meaningful statistical evaluation of the data, the results were combined for all experiments in which there was good evidence of protection by drug treatment against hippocampal damage (Example 7). Only experiments with positive results were combined to determine if the anatomical protection was associated with behavioral protection.

Results of the spontaneous alternation tests are summarized in Table 13 for experiments in which there was anatomical protection from doses of at least 0.1 µg of either compound. A chi square test on the combined data was significant at $p<0.01$. Combining treatment groups to examine each factor separately (e.g., all occluded vs. all unoccluded, regardless of drug treatment) indicated that each was significant by chi square at $p<0.05$; that is, (a) ischemia caused worse performance and (b) the level of performance was largely restored in treated animals.

While the invention has been described with reference to specific methods and embodiments, it will be appreciated that various modifications and changes may be made without departing from the invention.

---

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: SNX- 111

( x i ) SEQUENCE DESCRIPTION: SEQ ID NO:1:

```
Cys Lys Gly Lys Gly Ala Lys Cys Ser Arg Leu Met Tyr Asp Cys Cys
 1               5                  10                  15
Thr Gly Ser Cys Arg Ser Gly Lys Cys
                20                  25
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: SNX- 159

( x i ) SEQUENCE DESCRIPTION: SEQ ID NO:2:

```
Cys Lys Gly Lys Gly Ala Ser Cys His Arg Thr Ser Tyr Asp Cys Cys
 1               5                  10                  15
Thr Gly Ser Cys Asn Arg Gly Lys Cys
```

20                                      25

(2) INFORMATION FOR SEQ ID NO:3:

(i) SEQUENCE CHARACTERISTICS:
        (A) LENGTH: 27 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX- 124

(ix) FEATURE:
        (A) NAME/KEY: Modified-site
        (B) LOCATION: 4..5
        (D) OTHER INFORMATION: /note="where Xaa is
            hydroxyproline"

(ix) FEATURE:
        (A) NAME/KEY: Modified-site
        (B) LOCATION: 10..11
        (D) OTHER INFORMATION: /note="where Xaa is
            hydroxyproline"

(ix) FEATURE:
        (A) NAME/KEY: Modified-site
        (B) LOCATION: 21..22
        (D) OTHER INFORMATION: /note="where Xaa is
            hydroxyproline"

(xi) SEQUENCE DESCRIPTION: SEQ ID NO:3:

Cys Lys Ser Xaa Gly Ser Ser Cys Ser Xaa Thr Ser Tyr Asn Cys Cys
1               5                   10                  15

Arg Ser Cys Asn Xaa Tyr Thr Lys Arg Cys Tyr
            20                  25

(2) INFORMATION FOR SEQ ID NO:4:

(i) SEQUENCE CHARACTERISTICS:
        (A) LENGTH: 29 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX- 178

(ix) FEATURE:
        (A) NAME/KEY: Modified-site
        (B) LOCATION: 4..5
        (D) OTHER INFORMATION: /note="where Xaa is
            hydroxyproline"

(ix) FEATURE:
        (A) NAME/KEY: Modified-site
        (B) LOCATION: 7..8
        (D) OTHER INFORMATION: /note="where Xaa is
            hydroxyproline"

(xi) SEQUENCE DESCRIPTION: SEQ ID NO:4:

Cys Lys Ser Xaa Gly Thr Xaa Cys Ser Arg Gly Met Arg Asp Cys Cys
1               5                   10                  15

Thr Ser Cys Leu Leu Tyr Ser Asn Lys Cys Arg Arg Tyr 20                    25

(2) INFORMATION FOR SEQ ID NO:5:

(i) SEQUENCE CHARACTERISTICS:
        (A) LENGTH: 27 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-182

(ix) FEATURE:
        (A) NAME/KEY: Modified-site
        (B) LOCATION: 7..8
        (D) OTHER INFORMATION: /note="where Xaa is
            hydroxyproline"

(ix) FEATURE:
        (A) NAME/KEY: Modified-site
        (B) LOCATION: 4..5
        (D) OTHER INFORMATION: /note="where Xaa is
            hydroxyproline"

(xi) SEQUENCE DESCRIPTION: SEQ ID NO:5:

Cys Lys Pro Xaa Gly Ser Xaa Cys Arg Val Ser Ser Tyr Asn Cys Cys
1               5               10                      15

Ser Ser Cys Lys Ser Tyr Asn Lys Lys Cys Gly
            20                  25

(2) INFORMATION FOR SEQ ID NO:6:

(i) SEQUENCE CHARACTERISTICS:
        (A) LENGTH: 24 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-157

(ix) FEATURE:
        (A) NAME/KEY: Modified-site
        (B) LOCATION: 7..8
        (D) OTHER INFORMATION: /note="where Xaa is
            hydroxyproline"

(xi) SEQUENCE DESCRIPTION: SEQ ID NO:6:

Cys Arg Ser Ser Gly Ser Xaa Cys Gly Val Thr Ser Ile Cys Cys Gly
1               5               10                      15

Arg Cys Tyr Arg Gly Lys Cys Thr
            20

(2) INFORMATION FOR SEQ ID NO:7:

(i) SEQUENCE CHARACTERISTICS:
        (A) LENGTH: 27 amino acids
        (B) TYPE: amino acid
        (D) TOPOLOGY: both (ii) MOLECULE TYPE: peptide ( i i i ) HYPOTHETICAL: NO ( i v ) ANTI-SENSE: NO ( v i ) ORIGINAL SOURCE:
  ( C ) INDIVIDUAL ISOLATE: SNX- 185

( i x ) FEATURE:
  ( A ) NAME/KEY: Modified-site
  ( B ) LOCATION: 4..5
  ( D ) OTHER INFORMATION: /note="where Xaa is hydroxyproline"

( i x ) FEATURE:
  ( A ) NAME/KEY: Modified-site
  ( B ) LOCATION: 10..11
  ( D ) OTHER INFORMATION: /note="where Xaa is hydroxyproline"

( i x ) FEATURE:
  ( A ) NAME/KEY: Modified-site
  ( B ) LOCATION: 21..22
  ( D ) OTHER INFORMATION: /note="where Xaa is hydroxyproline"

( x i ) SEQUENCE DESCRIPTION: SEQ ID NO:7:

```
Cys Leu Ser Xaa Gly Ser Ser Cys Ser Xaa Thr Ser Tyr Asn Cys Cys
1               5                   10                  15
Arg Ser Cys Asn Xaa Tyr Ser Arg Lys Cys Arg
                20              25
```

( 2 ) INFORMATION FOR SEQ ID NO:8:

( i ) SEQUENCE CHARACTERISTICS:
    ( A ) LENGTH: 26 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: SNX- 183

( x i ) SEQUENCE DESCRIPTION: SEQ ID NO:8:

```
Cys Lys Leu Lys Gly Gln Ser Cys Arg Lys Thr Ser Tyr Asp Cys Cys
1               5                   10                  15
Ser Gly Ser Cys Gly Arg Ser Gly Lys Cys
                20              25
```

( 2 ) INFORMATION FOR SEQ ID NO:9:

( i ) SEQUENCE CHARACTERISTICS:
    ( A ) LENGTH: 25 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: SNX- 190

( x i ) SEQUENCE DESCRIPTION: SEQ ID NO:9:

```
Cys Lys Gly Ala Gly Ala Lys Cys Ser Arg Leu Met Tyr Asp Cys Cys
1               5                   10                  15
```

Thr Gly Ser Cys Arg Ser Gly Lys Cys
            20                    25

(2) INFORMATION FOR SEQ ID NO:10:

(i) SEQUENCE CHARACTERISTICS:
        (A) LENGTH: 25 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-191

(xi) SEQUENCE DESCRIPTION: SEQ ID NO:10:

Cys Ala Gly Lys Gly Ala Lys Cys Ser Arg Leu Met Tyr Asp Cys Cys
1               5                   10                  15

Thr Gly Ser Cys Arg Ser Gly Lys Cys
            20                    25

(2) INFORMATION FOR SEQ ID NO:11:

(i) SEQUENCE CHARACTERISTICS:
        (A) LENGTH: 26 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-193

(xi) SEQUENCE DESCRIPTION: SEQ ID NO:11:

Cys Lys Gly Lys Gly Ala Lys Cys Ser Arg Leu Met Tyr Asp Cys Cys
1               5                   10                  15

Thr Gly Ser Cys Arg Ser Gly Lys Cys Gly
            20                    25

(2) INFORMATION FOR SEQ ID NO:12:

(i) SEQUENCE CHARACTERISTICS:
        (A) LENGTH: 25 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-194

(ix) FEATURE:
        (A) NAME/KEY: Modified-site
        (B) LOCATION: 12..13
        (D) OTHER INFORMATION: /note="where Xaa is Norleucine"

(xi) SEQUENCE DESCRIPTION: SEQ ID NO:12:

Cys Lys Gly Lys Gly Ala Lys Cys Ser Arg Leu Xaa Tyr Asp Cys Cys
1               5                   10                  15

Thr Gly Ser Cys Arg Ser Gly Lys Cys
            20                      25

(2) INFORMATION FOR SEQ ID NO:13:

(i) SEQUENCE CHARACTERISTICS:
        (A) LENGTH: 25 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-195

(xi) SEQUENCE DESCRIPTION: SEQ ID NO:13:

Cys Lys Gly Lys Gly Ala Lys Cys Ser Arg Leu Met Tyr Asp Cys Cys
1               5                   10                  15

Thr Gly Ser Cys Arg Ser Gly Ala Cys
            20                  25

(2) INFORMATION FOR SEQ ID NO:14:

(i) SEQUENCE CHARACTERISTICS:
        (A) LENGTH: 27 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-196

(xi) SEQUENCE DESCRIPTION: SEQ ID NO:14:

Asn Cys Lys Gly Lys Gly Ala Lys Cys Ser Arg Leu Met Tyr Asp Cys
1               5                   10                  15

Cys Thr Gly Ser Cys Arg Ser Gly Lys Cys Gly
            20                  25

(2) INFORMATION FOR SEQ ID NO:15:

(i) SEQUENCE CHARACTERISTICS:
        (A) LENGTH: 27 amino acids
        (B) TYPE: amino acid
        (D) TOPOLOGY: both (ii) MOLECULE TYPE: peptide (iii) HYPOTHETICAL: NO (iv) ANTI-SENSE: NO (vi) ORIGINAL SOURCE:
        (C) INDIVIDUAL ISOLATE: SNX-197

(xi) SEQUENCE DESCRIPTION: SEQ ID NO:15:

Asn Ser Cys Lys Gly Lys Gly Ala Lys Cys Ser Arg Leu Met Tyr Asp
1               5                   10                  15

Cys Cys Thr Gly Ser Cys Arg Ser Gly Lys Cys
            20                  25

(2) INFORMATION FOR SEQ ID NO:16:

( i ) SEQUENCE CHARACTERISTICS:
  ( A ) LENGTH: 25 amino acids
  ( B ) TYPE: amino acid
  ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
  ( C ) INDIVIDUAL ISOLATE: SNX- 198

( x i ) SEQUENCE DESCRIPTION: SEQ ID NO:16:

Cys Lys Gly Lys Gly Ala Lys Cys Ser Arg Leu Met Tyr Asp Cys Cys
1               5                   10                  15

Thr Gly Ser Cys Ala Ser Gly Lys Cys
            20                  25

( 2 ) INFORMATION FOR SEQ ID NO:17:

( i ) SEQUENCE CHARACTERISTICS:
    ( A ) LENGTH: 25 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: SNX- 200

( x i ) SEQUENCE DESCRIPTION: SEQ ID NO:17:

Cys Lys Gly Lys Gly Ala Ala Cys Ser Arg Leu Met Tyr Asp Cys Cys
1               5                   10                  15

Thr Gly Ser Cys Arg Ser Gly Lys Cys
            20                  25

( 2 ) INFORMATION FOR SEQ ID NO:18:

( i ) SEQUENCE CHARACTERISTICS:
    ( A ) LENGTH: 25 amino acids
    ( B ) TYPE: amino acid
    ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
    ( C ) INDIVIDUAL ISOLATE: SNX- 201

( x i ) SEQUENCE DESCRIPTION: SEQ ID NO:18:

Cys Lys Gly Lys Gly Ala Lys Cys Arg Lys Thr Ser Tyr Asp Cys Cys
1               5                   10                  15

Thr Gly Ser Cys Arg Ser Gly Lys Cys
            20                  25

( 2 ) INFORMATION FOR SEQ ID NO:19:

( i ) SEQUENCE CHARACTERISTICS:
    ( A ) LENGTH: 26 amino acids
    ( B ) TYPE: amino acid
    ( D ) TOPOLOGY: both (  i  i  ) MOLECULE TYPE: peptide (  i  i  i  ) HYPOTHETICAL: NO (  i  v  ) ANTI-SENSE: NO (  v  i  ) ORIGINAL SOURCE:
     ( C ) INDIVIDUAL ISOLATE: SNX- 202

(  x  i  ) SEQUENCE DESCRIPTION: SEQ ID NO:19:

```
Cys Lys Leu Lys Gly Gln Ser Cys Ser Arg Leu Met Tyr Asp Cys Cys
1               5                   10                  15

Ser Gly Ser Cys Gly Arg Ser Gly Lys Cys
            20                  25
```

( 2 ) INFORMATION FOR SEQ ID NO:20:

(  i  ) SEQUENCE CHARACTERISTICS:
          ( A ) LENGTH: 27 amino acids
          ( B ) TYPE: amino acid
          ( D ) TOPOLOGY: both (  i  i  ) MOLECULE TYPE: peptide (  i  i  i  ) HYPOTHETICAL: NO (  i  v  ) ANTI-SENSE: NO (  v  i  ) ORIGINAL SOURCE:
          ( C ) INDIVIDUAL ISOLATE: SNX- 207

(  i  x  ) FEATURE:
          ( A ) NAME/KEY: Modified-site
          ( B ) LOCATION: 4..5
          ( D ) OTHER INFORMATION: /note="where Xaa is
               hydroxyproline"

(  i  x  ) FEATURE:
          ( A ) NAME/KEY: Modified-site
          ( B ) LOCATION: 21..22
          ( D ) OTHER INFORMATION: /note="where Xaa is
               hydroxyproline"

(  x  i  ) SEQUENCE DESCRIPTION: SEQ ID NO:20:

```
Cys Leu Ser Xaa Gly Ser Ser Cys Ser Arg Leu Met Tyr Asn Cys Cys
1               5                   10                  15

Arg Ser Cys Asn Xaa Tyr Ser Arg Lys Cys Arg
            20                  25
```

( 2 ) INFORMATION FOR SEQ ID NO:21:

(  i  ) SEQUENCE CHARACTERISTICS:
          ( A ) LENGTH: 27 amino acids
          ( B ) TYPE: amino acid
          ( D ) TOPOLOGY: both (  i  i  ) MOLECULE TYPE: peptide (  i  i  i  ) HYPOTHETICAL: NO (  i  v  ) ANTI-SENSE: NO (  v  i  ) ORIGINAL SOURCE:
          ( C ) INDIVIDUAL ISOLATE: SNX- 218

(  x  i  ) SEQUENCE DESCRIPTION: SEQ ID NO:21:

```
Cys Lys Ser Thr Gly Ser Ser Cys Ser Arg Leu Met Tyr Asn Cys Cys
1               5                   10                  15

Arg Ser Cys Asn Thr Tyr Ser Arg Lys Cys Arg
            20                  25
```

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: peptide fragment used in the claims ( x i ) SEQUENCE DESCRIPTION: SEQ ID NO:22:

Cys   Lys   Gly   Lys   Gly   Ala
    1                              5

( 2 ) INFORMATION FOR SEQ ID NO:23:

( i ) SEQUENCE CHARACTERISTICS:
        ( A ) LENGTH: 1 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: peptide fragment used in the claims ( x i ) SEQUENCE DESCRIPTION: SEQ ID NO:23:

Cys
    1

( 2 ) INFORMATION FOR SEQ ID NO:24:

( i ) SEQUENCE CHARACTERISTICS:
        ( A ) LENGTH: 8 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
        ( C ) INDIVIDUAL ISOLATE: peptide fragment used in the claims ( x i ) SEQUENCE DESCRIPTION: SEQ ID NO:24:

Tyr   Asp   Cys   Cys   Thr   Gly   Ser   Cys
    1                              5

( 2 ) INFORMATION FOR SEQ ID NO:25:

( i ) SEQUENCE CHARACTERISTICS:
        ( A ) LENGTH: 1 amino acids
        ( B ) TYPE: amino acid
        ( D ) TOPOLOGY: both ( i i ) MOLECULE TYPE: peptide ( i i i ) HYPOTHETICAL: NO ( i v ) ANTI-SENSE: NO 5,559,095

51

-continued

52

( v i ) ORIGINAL SOURCE:
            ( C ) INDIVIDUAL ISOLATE: peptide fragment used in the claims ( x i ) SEQUENCE DESCRIPTION: SEQ ID NO:25:

Arg
    1

( 2 ) INFORMATION FOR SEQ ID NO:26:

( i ) SEQUENCE CHARACTERISTICS:
            ( A ) LENGTH: 3 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
            ( C ) INDIVIDUAL ISOLATE: peptide fragment used in the claims ( x i ) SEQUENCE DESCRIPTION: SEQ ID NO:26:

Gly  Lys  Cys
    1

( 2 ) INFORMATION FOR SEQ ID NO:27:

( i ) SEQUENCE CHARACTERISTICS:
            ( A ) LENGTH: 7 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
            ( C ) INDIVIDUAL ISOLATE: peptide fragment used in the claims ( i x ) FEATURE:
            ( A ) NAME/KEY: Modified-site
            ( B ) LOCATION: 2..3
            ( D ) OTHER INFORMATION: /note="where Xaa is
                    hydroxyproline"

( x i ) SEQUENCE DESCRIPTION: SEQ ID NO:27:

Ser  Xaa  Gly  Ser  Ser  Cys  Ser
    1                   5

( 2 ) INFORMATION FOR SEQ ID NO:28:

( i ) SEQUENCE CHARACTERISTICS:
            ( A ) LENGTH: 10 amino acids
            ( B ) TYPE: amino acid
            ( D ) TOPOLOGY: both ( i i ) MOLECULE TYPE: peptide ( i i i ) HYPOTHETICAL: NO ( i v ) ANTI-SENSE: NO ( v i ) ORIGINAL SOURCE:
            ( C ) INDIVIDUAL ISOLATE: peptide fragment used in the claims ( i x ) FEATURE:
            ( A ) NAME/KEY: Modified-site
            ( B ) LOCATION: 9..10
            ( D ) OTHER INFORMATION: /note="where Xaa is
                    hydroxyproline"

( x i ) SEQUENCE DESCRIPTION: SEQ ID NO:28:

```
Tyr Asn Cys Cys Arg Ser Cys Asn Xaa Tyr
1               5                   10
```

It is claimed:

1. A method of reducing neuronal damage resulting from an ischemic condition in the central nervous system of a mammalian subject, comprising parenterally administering to the subject, at a time 6–24 hours following the onset of the ischemic condition, a pharmaceutically acceptable amount of an OCT peptide effective to inhibit voltage-gated calcium channels selectively in neuronal tissue, as evidenced by the ability of the OCT peptide to
  (a) bind to an MVIIA omega-conotoxin binding site in neuronal tissue with an affinity which is at least as great as that exhibited by any of the omega-conotoxins MVIIA, GVIA, TVIA and SNX-207 for said binding site; and
  (b) inhibit norepinephrine release at a given site in neuronal tissue with at least the same potency as that exhibited by any of the omega-conotoxins MVIIA, GVIA, TVIA and SNX-207 at said neuronal site.

2. The method of claim 1, wherein the binding affinity of the OCT peptide for an MVIIA binding site in neuronal tissue is characterized by competitive displacement of omega-conotoxin MVIIA from neuronal membranes.

3. The method of claim 1, wherein said binding is further characterized by a ratio of binding constants of the OCT peptide for a central nervous system omega-conotoxin MVIIA binding site and for a central nervous system SVIB binding site which is within a range of ratios for binding at said MVIIA site and said SVIB site measured for OCT peptides MVIIA, SNX-207, GVIA and TVIA.

4. The method of claim 1, wherein the OCT peptide is selected from the group consisting of omega-conotoxins SEQ ID NO: 01, SEQ ID NO: 03, SEQ ID NO: 07, and SEQ ID NO: 20.

5. A peptide having the sequence SEQ ID NO: 20, wherein t=a carboxy or amidated carboxyterminal group.

* * * * *